(12) United States Patent
Mallone et al.

(10) Patent No.: US 10,507,234 B2
(45) Date of Patent: Dec. 17, 2019

(54) METHODS AND PHARMACEUTICAL COMPOSITIONS FOR INDUCING IMMUNE TOLERANCE BY MUCOSAL VACCINATION WITH FC-COUPLED ANTIGENS

(71) Applicants: INSERM (INSTITUT NATIONAL DE LA SANTÉ ET DE LA RECHERCHE MÉDICALE), Paris (FR); UNIVERSITÉ PARIS DESCARTES, Paris (FR); CENTRE NATIONAL DE LA RECHERCHE SCIENTIFIQUE (CNRS), Paris (FR); UNIVERSITÉ PIERRE ET MARIE CURIE (PARIS 6), Paris (FR); UNIVERSITÉ PARIS DIDEROT—PARIS 7, Paris (FR); UNIVERSITÉ PARIS-SUD, Orsay (FR); SORBONNE UNIVERSITE, Paris (FR)

(72) Inventors: Roberto Mallone, Paris (FR); Slobodan Culina, Paris (FR); Nimesh Gupta, Paris (FR); Sebastien Lacroix-Desmazes, Paris (FR)

(73) Assignees: INSERM (INSTITUT NATIONAL DE LA SANTE ET DE LA RECHERCHE MEDICALE), Paris (FR); UNIVERSITE PARIS DESCARTES, Paris (FR); UNIVERSITE PIERRE ET MARIE CURIE (PARIS 6), Paris (FR); UNIVERSITE PARIS DIDEROT—PARIS 7, Paris (FR)

(*) Notice: Subject to any disclaimer, the term of this patent is extended or adjusted under 35 U.S.C. 154(b) by 11 days.

(21) Appl. No.: 15/745,273

(22) PCT Filed: Jul. 13, 2016

(86) PCT No.: PCT/EP2016/066690
§ 371 (c)(1),
(2) Date: Jan. 16, 2018

(87) PCT Pub. No.: WO2017/012959
PCT Pub. Date: Jan. 26, 2017

(65) Prior Publication Data
US 2018/0207250 A1     Jul. 26, 2018

(30) Foreign Application Priority Data
Jul. 17, 2015 (EP) .................................. 15306169

(51) Int. Cl.
*A61K 39/00* (2006.01)
*A61P 37/06* (2006.01)

(52) U.S. Cl.
CPC .......... *A61K 39/0008* (2013.01); *A61P 37/06* (2018.01); *A61K 2039/542* (2013.01); *A61K 2039/577* (2013.01); *A61K 2039/6056* (2013.01)

(58) Field of Classification Search
CPC .......... A61K 39/0008; A61K 2039/542; A61K 2039/6056; A61K 2039/577; A61P 37/06
See application file for complete search history.

(56) References Cited

U.S. PATENT DOCUMENTS

| | | | | |
|---|---|---|---|---|
| 6,086,875 A | * | 7/2000 | Blumberg | A61K 39/385 424/134.1 |
| 2012/0178139 A1 | * | 7/2012 | Hubbell | A61K 9/1075 435/188 |
| 2012/0213780 A1 | * | 8/2012 | Zhu | C07K 14/005 424/134.1 |

OTHER PUBLICATIONS

Slobodan Culina et al: "Materno-Fetal Transfer of Preproinsulin Through the Neonatal Fc Receptor Prevents Autoimmune Diabetes", Diabetes, American Diabetes Association, US, vol. 64, No. 10, Apr. 27, 2015 (Apr. 27, 2015), pp. 3532-3542, (Year: 2015).*

(Continued)

*Primary Examiner* — Jana A Hines
(74) *Attorney, Agent, or Firm* — W&C IP

(57) ABSTRACT

The present invention relates to methods and pharmaceutical compositions of inducing immune tolerance by mucosal vaccination with Fc-coupled antigens. In particular, the present invention relates to a method for inducing tolerance to one antigen of interest in a subject in need thereof, comprising the mucosal administration to the subject of a therapeutically effective amount of a recombinant chimeric construct comprising a FcRn targeting moiety and an antigen-containing moiety.

13 Claims, 12 Drawing Sheets

(56) References Cited

OTHER PUBLICATIONS

Figure 1:
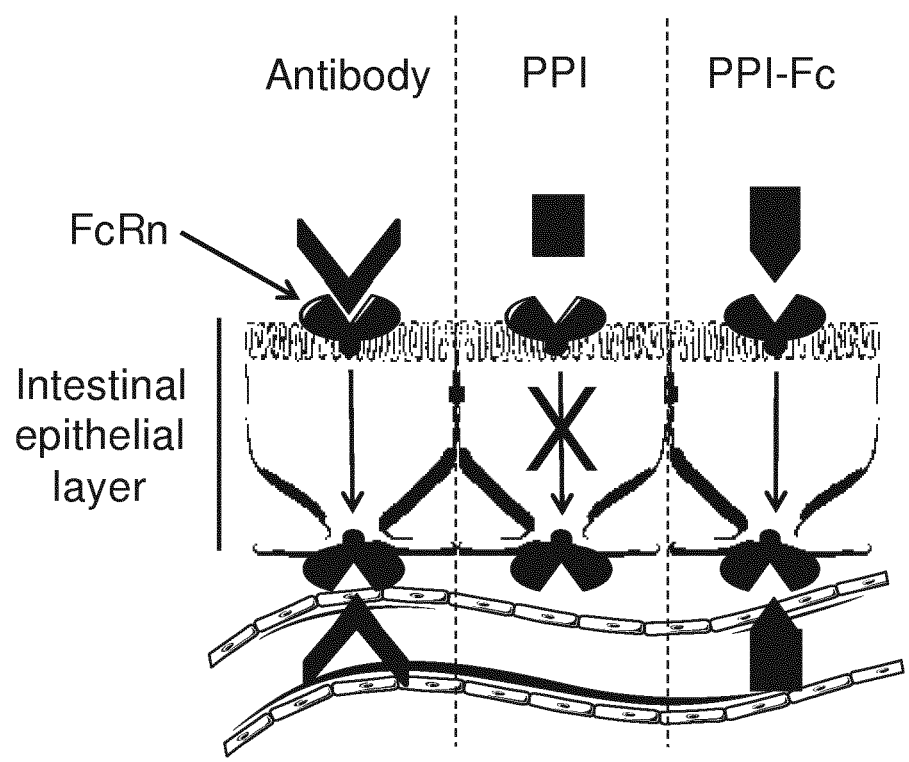

Slobodan Culina et al: "Materno-Fetal Transfer of Preproinsulin Through the Neonatal Fc Receptor Prevents Autoimmune Diabetes", Diabetes, American Diabetes Association, US, vol. 64, No. 10, pp. 3532-3542, Apr. 27, 2015.

\* cited by examiner

METHODS AND PHARMACEUTICAL COMPOSITIONS FOR INDUCING IMMUNE TOLERANCE BY MUCOSAL VACCINATION WITH FC-COUPLED ANTIGENS

FIELD OF THE INVENTION

The present invention relates to methods and pharmaceutical compositions of inducing immune tolerance by mucosal vaccination with Fc-coupled antigens.

BACKGROUND OF THE INVENTION

Autoimmune diseases represent a major health concern. For example, type 1 diabetes (T1D) is an autoimmune disease mediated by autoreactive T cells that recognize β-cell antigens (Ags), leading to destruction of pancreatic islets. A major problem in T1D management is its late diagnosis. This typically takes place after a variable period of subclinical, silent autoimmunity, once a significant proportion of β cells have already been destroyed. The resulting insulin deficiency leads to hyperglycemia and clinical onset. Hence, T1D prevention and treatment should target the underlying autoimmune mechanisms rather than its metabolic consequences, as done today with insulin replacement therapies. However, immunotherapies aimed at blunting β-cell autoimmunity need to have an excellent safety profile, since T1D mostly affects children and young adults and is not life-threatening in the short term.

β-cell Ag-specific therapies are therefore attractive in light of their selectivity and safety, compared to treatments broadly targeting the T-cell subsets involved in disease[1]. Such therapies are administered in the form of vaccines comprising the β-cell Ags whose immune recognition mediates islet destruction. These vaccines are formulated to achieve immune outcomes that are opposite to those pursued with classical vaccination, i.e. to neutralize rather than to stimulate the T-cell responses against the administered Ags—instating a condition known as immune tolerance. Clinical trials have however been deceiving[2-4]. Several attempts have focused on tolerogenic vaccination with β-cell Ags derived from insulin and its precursor preproinsulin (PPI), since this is the initiating Ag in the non-obese diabetic (NOD)[5,6] mouse and likely also in humans[2]. A recent trial employing intranasal insulin administration to halt autoimmune β-cell destruction in new-onset T1D patients with slowly evolving disease did not result in significant β-cell preservation, despite evidence that insulin-specific immune tolerance was successfully induced[7]. These results suggest that we may need to intervene earlier, before significant β-cell loss and before autoimmune progression. While PPI recognition initiates the autoimmune cascade, subsequent β-cell destruction releases additional Ags that are further recognized (a phenomenon known as Ag spreading), thus making tolerance restoration vis-à-vis of the sole PPI insufficient.

The same problem is encountered in prevention trials using insulin vaccination, where the safety issue is even more critical for treating at-risk subjects who are not yet diabetic. Despite absence of clinical disease, selection of at-risk subjects is based on positivity for multiple auto-antibodies (auto-Abs), which witness an autoimmune reaction that already involves several Ags[3, 8, 9]. Recent studies further suggest that β-cell autoimmunity initiates very early, as the median age at auto-Ab seroconversion was only 9-18 months in large prospective cohorts of genetically at-risk children[10,11]. Insulin Ag-specific prevention strategies should therefore be implemented at a much earlier stage, in at-risk children (i.e. first-degree relatives of T1D patients) carrying a high HLA-associated genetic risk of disease but with no signs of active autoimmunity (i.e. auto-Ab-)[12,13].

The perinatal period offers such opportunities not only in terms of timing, but also because it is characterized by immune responses to introduced Ags that are biased towards tolerogenic outcomes. Indeed, Ag introduction during fetal and neonatal life results in Ag-specific immune tolerance persisting during adulthood[14-16]. A key role in this process is played by central tolerance, a process taking place in the thymus in which developing T cells are challenged with ectopically expressed self-tissue Ags such as PPI. Their recognition leads to elimination of autoreactive pathogenic T effector cells (Teffs) and to positive selection of T regulatory cells (Tregs)[17]. This process is very active during the perinatal period and leads to the definition of immunological self that later imprints peripheral immune responses. The 'immune self-image' presented in the thymus is however incomplete, because the self Ag repertoire is only partially expressed[17]. Indeed, defective central tolerance is the first checkpoint in T1D progression. Some autoreactive Teffs escape thymic selection and can later be activated in the periphery and perpetrate islet destruction. Supporting this notion, the NOD mouse model of T1D develops accelerated diabetes when PPI expression is abolished in the thymus (Ins2−/− NOD mice)[18,19]. Second, human INS polymorphic variants predispose to T1D by decreasing INS expression in the thymus[20].

However, this knowledge has not translated into therapeutic strategies aimed at boosting central tolerance ab initio. All tolerogenic vaccination approaches explored to date using the subcutaneous, intranasal or oral route are targeted on peripheral tolerance and aim at blunting the pathogenic potential of autoreactive Teffs and/or at enhancing Treg activity[1]. If we could instead introduce self Ags such as PPI in the thymus during the perinatal period, we could boost the T-cell selection process and intervene on the very first step in autoimmune progression.

The present invention relates to the use of Ags fused with the Fc portion of an IgG to induce immune tolerance by mucosal vaccination. Fc-fusion proteins currently represent 20% of all Ab-based medicines with FDA approval and are actively investigated in a variety of settings because addition of an Fc moiety increases the half-life of protein therapeutics. Binding of the Fc domain to the neonatal Fc receptor (FcRn) expressed in endothelial cells leads to their transient intracellular sequestration and slow release in the circulation. The FcRn is a heterodimer composed of a major histocompatibility complex (MHC) Class-I-like heavy chain and β2-microglobulin[21]. The interaction between IgG and FcRn requires an acidic pH (<6.5) and is inefficient at a physiological pH (7.4)[21]. It occurs in a 1:2 stoichiometry, with one IgG binding to two FcRn molecules via the FcRn heavy chains and the CH2-CH3 portion of the Fc domain of IgG[22].

Besides endothelial cells, the FcRn is expressed in several other tissues and cells[23], including the placental syncytiotrophoblast or yolk sac of mammals, the liver, intestinal, bronchial, renal (proximal convoluted tubule), genital, ocular and choroid plexus epithelia, renal podocytes; the skin (hair follicles, sebaceous glands, epidermal keratinocytes and melanocytes); hematopoietic cells such as dendritic cells, monocytes and macrophages (including macrophages in the lamina propria of the small intestine)[24]. In the respiratory tract, the FcRn is predominantly found in the bronchial epithelium of upper and central airways. In the human digestive tract, FcRn is expressed in epithelial cells of the stomach, the small intestine (duodenum, jejunum and ileum) and the colon[25-27]. There is an increasing proximal-distal gradient of mucosal FcRn mRNA and protein expression in the intestinal tract, with expression being the lowest in the duodenum-jejunum and highest in the proximal colon. This expression gradient correlates with the efficiency of in vitro monoclonal Ab (mAb) transcytosis for these different intestinal regions, with systemic entry occurring via the lymphatics[27]. The same expression gradient is found in cynomolgus monkeys, in which serum mAb levels were greater after ileum-proximal colon infusion than after administration into the duodenum-jejunum[27]. Taken together, the FcRn expression and mAb uptake patterns suggest that the ileum-proximal colon is the region where most of the mAb is transcytosed through the FcRn.

In more recent years, the application of Fc-coupled agents has therefore been extended to strategies aimed at delivering bioactive molecules using less invasive administration route, namely the gastrointestinal or pulmonary route. Typically, IgG are endocytosed on the apical membrane of epithelial cells and bind to FcRn at the acidic pH present in endosomes. The vesicle then fuses again with the basolateral membrane, where the extracellular neutral pH promotes the dissociation of IgG from FcRn. Importantly, FcRn-mediated transport of IgG is bidirectional (i.e. both from the apical and basolateral membrane of epithelial cells)[28] and occurs rapidly, within 1 h after IgG addition in in vitro Transwell experiments[26]. Examples of Fc-coupled agents explored for oral delivery include Fc-coupled follicle-stimulating hormone (FSH)[29], IgG mAbs[27] and Fc-coated nanoparticles containing bioactive molecules such as insulin[30]. Overall, the systemic bioavailability achieved by oral administration of Fc-coupled agents is relatively limited. Examples of Fc-coupled agents explored for pulmonary delivery include Fc-coupled erythropoietin[31-33] and Fc-coupled FSH[29].

Hence, Fc-coupled agents have been used to increase the half-life of systemically administered therapeutic proteins and to facilitate their systemic delivery through the intestinal or bronchial route. We here propose to use the same strategy to induce immune tolerance. To this end, Ags can be modified by fusing them to the Fc portion of an IgG1, thus allowing the resulting Ag-Fc proteins to interact with the FcRn and cross mucosal barriers. This is the same pathway that physiologically delivers maternal IgG to foetuses (through the placenta) and to newborns (through the gut, during lactation)[21], thus providing passive IgG protection during the intrauterine period and the first 6 months of life, when IgG production is not yet operational. This concept was first validated using the transplacental route of transfer and indicated that Fc-fused Ags intravenously administered to pregnant mice reach the fetal thymus in an FcRn-dependent manner and promote the generation of Ag-specific Tregs, leading to Ag-specific tolerance[24]. When applied to T1D mouse models, PPI-Fc transplacental transfer protects the offspring from diabetes development later in life[35,36]. A single 100 μg PPI-Fc dose intravenously administered to pregnant PPI T-cell receptor-transgenic G9C8 NOD mice (in which all T cells recognize a $PPI_{B15-23}$ epitope[37]) is transplacentally transferred and protects the offspring from diabetes, without inducing metabolic or other adverse effects. This transfer is Fc- and FcRn-dependent. Diabetes protection is associated with peripheral PPI-reactive $CD8^+$ Teffs displaying impaired cytotoxicity and with increased thymic-derived neuropilin-1 $(NRP1/CD304)^+$ $CD4^+$ Tregs secreting the regulatory cytokine transforming growth factor (TGF)-β. PPI-Fc reaches the thymus carried by migratory $(CD8^{lo}CD11b^+SIRP\alpha^+)$ dendritic cells (DCs) and diabetes protection is lost when migration is inhibited by early administration of anti-vascular cell adhesion molecule (VCAM)-1 Abs. Importantly, diabetes protection is also active in polyclonal NOD mice[35]. Although successful, this strategy remains invasive for autoimmune diseases like T1D that we cannot predict with certainty early enough, a fortiori prenatally. Such strategies applied to pregnant women may be considered to carry a risk for the fetus and the mother unacceptable in front of diseases that are in most cases not life-threatening in the short term and that may or may not develop.

SUMMARY OF THE INVENTION

The present invention relates to methods and pharmaceutical compositions for inducing immune tolerance by mucosal vaccination with Fc-coupled Ags. In particular, the present invention is defined by the claims.

DETAILED DESCRIPTION OF THE INVENTION

Now the inventors have evidence that antigen-Fc orally administered directly to newborn mice induces profound T-cell modifications suggestive of tolerance induction. The inventors therefore propose to explore its suitability for preventing or treating diseases and conditions such as autoimmune diseases, allergic diseases and immune responses against antigens that are exogenously administered.

Thus, one object of the present invention relates to a method for inducing tolerance to one antigen of interest in a subject in need thereof comprising the mucosal administration to the subject of a therapeutically effective amount of a recombinant chimeric construct comprising a FcRn targeting moiety and an antigen-containing moiety.

As used herein, the term "antigen" has its general meaning in the art and generally refers to a substance or fragment thereof that is recognized and selectively bound by an antibody or by a T cell antigen receptor, resulting in induction of an immune response. Antigens according to the invention are typically, although not exclusively, peptides and proteins. Antigens may be natural or synthetic and generally induce an immune response that is specific for that antigen. Other non-protein antigens recognized by specialized T-cell subsets such as natural killer T cells[38-40] and mucosal-associated invariant T cells[41-43] may also be considered.

In some embodiments, the antigen is an auto-antigen. As used herein, the term "auto-antigen" means any self-antigen arising from the own body tissues which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

In some embodiments, the antigen is an allergen. As used herein, the term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

In some embodiments, the antigens are molecules that are exogenously administered for therapeutic or other purposes and may trigger an unwanted immune response. While frequently neutralising the biological activity that said molecules are meant to induce, such immune responses may have additional deleterious effects unrelated to the purpose for which the molecules were originally administered. Examples of this kind include immune reactions against therapeutic clotting factor VIII in haemophilia A or factor IX in haemophilia B, against different enzymes in congenital enzymopathies and, more in general, during any kind of replacement therapies in the context of genetic deficiencies. Allo-immunization responses against antigens expressed by tissues or hematopoietic and/or blood cells transplanted into an individual are equally considered.

The term "tolerance," as used herein, refers to a failure to respond, or a reduced response, to an antigen (including auto-antigens, allergens and endogenously administered molecules). This may mean that a productive (immunogenic) response is not induced upon endogenous or exogenous exposure to said antigen. This response may be replaced, in part or completely, by a tolerogenic response, i.e. an active process that further limits immunogenic responses. Examples of tolerogenic responses include, but are not limited to, generation of T regulatory cells, elimination of effector (conventional) T cells by apoptosis or their neutralization by anergy, and skewing of T cells and other immune cells towards phenotypes favouring a state of tolerance, e.g. production of regulatory cytokines such as interleukin-10 and TGF-β and of other anti-inflammatory mediators and downregulated expression of co-stimulatory molecules. These immunological concepts are well known to the skilled in the art.

In some embodiments, the subject is human, but treatment of other animals is also encompassed. In some embodiments, the subject is an adult. In some embodiments, the subject is a pregnant woman. In some embodiments, the subject is a child. In some embodiments, the subject is a child that is less than 18, 17, 16, 15, 14, 13, 12, 11, 10, 9, 8, 7, 6, 5, 4, 3, 2 or 1 year(s) old. In some embodiments, the subject is a newborn. In some embodiments, the subject is a neonate. As used herein, a "neonate" is a newborn that is less than about 28-day-old. In some embodiments, the subject is a pregnant woman that may give birth to a child at risk of developing a disease.

In some embodiments, the subject is predisposed or believed to be predisposed to developing, or has already developed or is developing, at least one symptom of a disease or condition caused by inappropriate or unwanted immune system activity against an antigen. The subject may be identified or diagnosed as having done so or as likely to do so based on a variety of factors, for example, family history and/or genetic testing of e.g. the mother and/or father, siblings, other relatives (grandparents, aunts, uncles, cousins, etc.), presence of other disease biomarkers such as (auto)antibodies directed against different (self-)antigens. Generally, the subject is known to have a genetic predisposition to development of an autoimmune disease, an allergy or other unwanted immune response. By "is known to have a genetic predisposition", we mean that one or both parents or siblings may have the disease or condition, and/or are known to be carriers of gene(s) that is/are associated with the disease or condition, so that the statistical probability of the subject having or developing the disease is at least 1, 5, 10, 20, 30, 40, 50, 60, 70, 80, 90%, or is 100%. The determination may be based on observation of the health of the parents, siblings or of the subject, or on genetic testing of the same and identification of a gene or genes in a form known to be associated with or to cause the disease or condition, e.g. to have a particular sequence such as an allele, mutation, insertion, deletion, etc. The risk of disease may or may not also be confirmed by genotyping subject's cells and/or by assessing them by suitable biomarkers, including non-genetic biomarkers such as, by way of example, antibodies and other immune phenotypes or epigenetic modifications. Those of skill in the art will also recognize that such genetic traits may not be "all or nothing", in that gene dosage may apply. Nevertheless, if a subject is deemed to be at risk, and if the life of a subject can be lengthened or improved by the practice of the present methods, then the subject is a viable candidate for treatment.

In some embodiments, the subject is predisposed or believed to be predisposed to developing, or has already developed or is developing an autoimmune disease. As used herein, the term "autoimmune disease" refers to the presence of an autoimmune response (an immune response directed against an auto- or self-antigen) in a subject. Autoimmune diseases include diseases caused by a breakdown of self-tolerance such that the adaptive immune system, in concert with cells of the innate immune system, responds to self-antigens and mediates cell and tissue damage. In some embodiments, autoimmune diseases are characterized as being a result of, at least in part, a humoral and/or cellular immune response. Examples of autoimmune disease include, without limitation, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticaria, axonal and neuronal neuropathies, Behcet's disease, bullous pemphigoid, autoimmune cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, hypergammaglobulinemia, idiopathic thrombocytopenic purpura (ITP), IgA nephropathy, IgG4-related sclerosing disease, immunoregulatory lipoproteins, inclusion body myositis, inflammatory bowel disease, insulin-dependent diabetes (type 1), interstitial cystitis, juvenile arthritis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), Mooren's ulcer, Mucha-Habermann disease, multiple sclerosis, myasthenia gravis, myositis, narcolepsy, neuromyelitis optica (Devic's), autoimmune neutropenia, ocular cicatricial pemphigoid, optic neuritis, palindromic rheumatism, PANDAS (Pediatric Autoimmune Neuropsychiatric Disorders Associated with Streptococcus), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom's macroglobulinemia (WM), and Wegener's granulomatosis [Granulomatosis with Polyangiitis (GPA)]. In some embodiments, the autoimmune disease is selected from the group consisting of rheumatoid arthritis, type 1 diabetes, systemic lupus erythematosus (lupus or SLE), myasthenia gravis, multiple sclerosis, scleroderma, Addison's Disease, bullous pemphigoid, pemphigus vulgaris, Guillain-Barré syndrome, Sjogren syndrome, dermatomyositis, thrombotic thrombocytopenic purpura, hypergammaglobulinemia, monoclonal gammopathy of undetermined significance (MGUS), Waldenstrom's macroglobulinemia (WM), chronic inflammatory demyelinating polyradiculoneuropathy (CIDP), Hashimoto's Encephalopathy (HE), Hashimoto's Thyroiditis, Graves' Disease, Wegener's Granulomatosis [Granulomatosis with Polyangiitis (GPA)]. In some embodiments, the autoimmune disease is type 1 diabetes.

In some embodiments, the subject is predisposed or believed to be predisposed to developing, or has already developed or is developing an allergy. As used herein, the term "allergy" generally refers to an inappropriate immune response characterized by inflammation and includes, without limitation, food allergies, respiratory allergies and other allergies causing or with the potential to cause a systemic response such as, by way of example, Quincke's oedema and anaphylaxis. The term encompasses allergy, allergic disease, hypersensitive associated disease or respiratory disease associated with airway inflammation, such as asthma or allergic rhinitis. In some embodiments, the method of the present invention is effective in preventing, treating or alleviating one or more symptoms related to anaphylaxis, drug hypersensitivity, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD). Hypersensitivity associated diseases or disorders that may be treated by the method of the present invention include, but are not limited to, anaphylaxis, drug reactions, skin allergy, eczema, allergic rhinitis, urticaria, atopic dermatitis, dry eye disease [or otherwise referred to as Keratoconjunctivitis sicca (KCS), also called keratitis sicca, xerophthalmia], contact allergy, food allergy, allergic conjunctivitis, insect venom allergy and respiratory diseases associated with airway inflammation, for example, IgE mediated asthma and non-IgE mediated asthma. The respiratory diseases associated with airway inflammation may include, but are not limited to, rhinitis, allergic rhinitis, bronchial asthma, allergic (extrinsic) asthma, non-allergic (intrinsic) asthma, occupational asthma, atopic asthma, exercise induced asthma, cough-induced asthma, acute respiratory distress syndrome (ARDS) and chronic obstructive pulmonary disease (COPD).

In some embodiments, the subject is predisposed or believed to be predisposed to developing, or has already developed or is developing an immune reaction against molecules that are exogenously administered for therapeutic or other purposes and may trigger an unwanted immune response. Non-limiting examples of this kind include immune reactions against replacement therapeutics in the context of genetic deficiencies, which include, but are not limited to, haemophilia A, haemophilia B, congenital deficiency of other clotting factors such as factor II, prothrombin and fibrinogen, primary immunodeficiencies (e.g. severe combined immunodeficiency, X-linked agammaglobulinemia, IgA deficiency), primary hormone deficiencies such as growth hormone deficiency and leptin deficiency, congenital enzymopathies and metabolic disorders such as disorders of carbohydrate metabolism (e.g. sucrose-isomaltase deficiency, glycogen storage diseases), disorders of amino acid metabolism (e.g. phenylketonuria, maple syrup urine disease, glutaric acidemia type 1), urea cycle disorders (e.g. carbamoyl phosphate synthetase I deficiency), disorders of organic acid metabolism (e.g. alcaptonuria, 2-hydroxyglutaric acidurias), disorders of fatty acid oxidation and mitochondrial metabolism (e.g. medium-chain acyl-coenzyme A dehydrogenase deficiency), disorders of porphyrin metabolism (e.g. porphyrias), disorders of purine or pyrimidine metabolism (e.g. Lesch-Nyhan syndrome), disorders of steroid metabolism (e.g. lipoid congenital adrenal hyperplasia, congenital adrenal hyperplasia), disorders of mitochondrial function (e.g. Kearns-Sayre syndrome), disorders of peroxisomal function (e.g. Zellweger syndrome), lysosomal storage disorders (e.g. Gaucher's disease, Niemann Pick disease). In the case of genetic deficiencies, the proposed method may not only allow to reinstate immune tolerance against the replacement therapeutics that are used to treat the disease, but also reinstate the biological activity for which said therapeutics are administered. Other therapeutics for which said method may be suitable to limit undesired immune responses include other biological agents such as, by way of example, cytokines, monoclonal antibodies, receptor antagonists, soluble receptors, hormones or hormone analogues, coagulation factors, enzymes, bacterial or viral proteins. For example, haemophilic children can be treated prophylactically with periodic coagulation factor (e.g. factor VIII) replacement therapy, which decreases the chance of a fatal bleed due to injury. In addition to the expense and inconvenience of such treatment, repeated administration results in inhibitor antibody formation in some patients against the coagulation factor. If the antibodies in these patients are low titer antibodies, patients are treated with larger doses of blood coagulation factors. If the antibodies are high titer antibodies, treatment regimens for these patients become much more complex and expensive. In some embodiments, the therapeutic protein is produced in the subject following gene therapy suitable e.g. for the treatment of congenital deficiencies. Gene therapy typically involves the genetic manipulation of genes responsible for disease. One possible approach for patients, like those with haemophilia deficient for a single functional protein, is the transmission of genetic material encoding the protein of therapeutic interest. However, the repeated administration of gene therapy vectors, such as viral vectors, may also trigger unwanted immune responses against the therapeutic protein introduced in the vector and/or against other components of the vector. Thus, the method of the present invention can be suitable for overcoming the body's immune response to gene therapy vectors such as viral vectors. Viral vectors are indeed the most likely to induce an immune response, especially those, like adenovirus and adeno-associated virus (AAV), which express immunogenic epitopes within the organism. Various viral vectors are used for gene therapy, including, but not limited to, retroviruses for X-linked severe combined immunodeficiency (X-SCID); adenoviruses for various cancers; adeno-associated viruses (AAVs) to treat muscle and eye diseases; lentivirus, herpes simplex virus and other suitable means known in the art.

In some embodiments, the subject is predisposed or believed to be predisposed to developing, or has already developed or is developing an immune reaction against a grafted tissue or grafted hematopoietic cells or grafted blood cells. Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder. The method of the present invention is also particularly suitable for preventing or suppressing an immune response associated with rejection of a donor tissue, cell, graft, or organ transplant by a recipient subject. Graft-related diseases or disorders include graft versus host disease (GVHD), such as associated with bone marrow transplantation, and immune disorders resulting from or associated with rejection of organ, tissue, or cell graft transplantation (e.g., tissue or cell allografts or xenografts), including e.g., grafts of skin, muscle, neurons, islets, organs, parenchymal cells of the liver, etc. Thus the method of the invention is useful for preventing Host-Versus-Graft-Disease (HVGD) and Graft-Versus-Host-Disease (GVHD). The chimeric construct may be administered to the subject before, during and/or after transplantation (e.g., at least one day before transplantation, at least one day after transplantation, and/or during the transplantation procedure itself). In some embodiments, the chimeric construct may be administered to the subject on a periodic basis before and/or after transplantation.

In some embodiments, the method of the present invention is particularly suitable for the treatment of autoimmune diseases, allergic diseases and congenital deficiencies.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., daily, weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

According to the present invention, the chimeric construct comprises an antigen-containing moiety. This moiety comprises an antigenic molecule or a portion of an antigenic molecule for which is it desired to generate immune tolerance, and may comprise a plurality of antigens or portions of antigens. Preferably, the antigen is a protein, a polypeptide or a peptide. In some embodiments, the antigen-containing moiety comprises one or more known epitopes of interest, e.g. regions or residues of the antigen which are known to elicit an immune response. Alternatively, putative epitopes and antigenic regions may be selected based on a likelihood of antigenicity due to accessibility, surface exposure, charge, amino acid sequence etc. e.g. using prediction software programs well known in the art. Typically, the antigen-containing moiety comprises contiguous sequences of the primary sequence of an antigen. Alternatively, sufficient residues of the antigen may be present so that secondary and tertiary structure is at least partially preserved, and antigenic regions are present that are not necessarily contiguous in primary sequence but are adjacent after folding of the molecule or generated by fusion of non-adjacent antigen sequences, as described for different 'hybrid' epitopes. The antigenic moiety of the construct may contain an epitope or multiple epitopes from one or from more than one antigen of interest. Multiple epitopes may be continuous in the construct sequence or separated by appropriate linkers. The multiple epitopes may be the same, e.g. multiple copies of the same epitope may be present; or the epitopes may be different, e.g. single or multiple copies of two or more different epitopes may be present. The epitopes may be "different" from (may differ from) each other either by virtue of originating from different antigenic molecules, or by originating from different parts of the same antigenic molecule, or both, e.g. the same region of an antigen from several different variants may be used. Combinations of the above may also be present. Post-translationally modified epitopes or epitopes generated by alternative splicing may equally be included. The amino acid sequence of the antigen-containing moiety may have 100% identity to that of a protein, polypeptide or peptide that is a natural antigen.

Alternatively, the antigenic moiety may comprise a portion (e.g. at least about 10, 15, 20, 25, 30, 35, 40, 45, 50, 55, 60, 65, 70, 75, 80, 85, 90, 95% or more) of the residues of a native sequence to which immune tolerance is desired. Further, the amino acid sequence in the antigenic moiety may be the same primary sequence as that of a native protein antigen, or may be a variant thereof with at least about 50, 55, 60, 65, 70, 75, 80, 85, 90, 95% or more identity or homology to the native protein sequence, or to the portion of the native sequence on which it is based.

In some embodiments, the antigen-containing moiety derives from preproinsulin (PPI), glutamic acid decarboxylase (GAD), insulinoma-associated protein 2 (IA-2), islet-specific glucose-6-phosphatase catalytic-subunit-related protein (IGRP), zinc transporter 8 (ZnT8), pre-pro-islet amyloid polypeptide (ppIAPP), 78 kDa glucose-regulated protein [GRP78 and its precursor; also known as heat shock 70 kDa protein 5 (HSPA5)], dystrophia myotonica kinase (DMK) and chromogranin A for T1D; myeloperoxydase and proteinase 3 for granulomatosis with polyangiitis; myelin oligodendrocyte glycoprotein (MOG), myelin basic protein (MBP) and proteolipid protein (PLP) in multiple sclerosis; various synovial antigens such as vimentin, nuclear ribonucleoprotein-A2 (RA33), fibrinogen, alpha-enolase for rheumatoid arthritis; tissue transglutaminase and gliadins in celiac disease. Post-translationally modified epitopes, alternative splice isoforms and hybrid peptides derived from said antigens—alone or in combination with other antigens—are equally included. Canonical antigens or antigen isoforms that are not properly expressed in the thymus may be particularly suitable to this end. Examples of antigen moieties are derived from the above said protein following processing by antigen-presenting cells—including dendritic cells—and presentation in the context of different human leukocyte antigen (HLA) Class I or Class II molecules. Therefore, said peptide antigens are different depending not only on their source antigen, but also on the HLA molecules by which they are presented. For example, a list of T1D-associated peptide antigens for both mouse and human can be found in DiLorenzo et al., Clin. Exp. Immunol. 148:1, 2007[44].

In some embodiments, the antigen-containing moiety derives from an allergen. Allergens include, but are not limited to. phospholipase A2 (API ml) associated with severe reactions to bee, Derp-2, Der p 2, Der f, Der p 5 and Der p 7 associated with reaction against the house-dust mite *Dermatophagoides pteronyssinus*, the cockroach allergen Bla g 2 and the major birch pollen allergen Bet v 1.

In some embodiments, the antigen-containing moiety derives from a therapeutic protein. The term "therapeutic proteins" as used herein refers to protein or peptide compounds of any aminoacid length that are administered or are planned to be administered in vivo to human subjects to achieve a therapeutic effect. Examples of such therapeutic proteins are, but are not limited to, antibodies of different species (either in their native form or partially/fully humanized), cytokines, receptor antagonists, soluble receptors, hormones or hormone analogues, coagulation factors, enzymes, bacterial or viral proteins. Example of therapeutic applications wherein the therapeutic protein can be suitable include, without being limited to, cytokine- and antibody-based immune therapies, hormone replacement therapies and replacement therapies for coagulation factors (e.g., factor VIII in haemophilia A) or enzymatic deficits (e.g., beta-glucuronidase in mucopolysaccharidosis VII). In all these situations, mounting of immunogenic responses against the administered protein is not desirable, as this would be counterproductive for achieving the desired therapeutic effect (e.g., side effects such as cytokine release syndromes; or neutralization/degradation of the therapeutic protein).

As used herein, the term "neonatal Fc receptor" or "FcRn" has its general meaning in the art and refers to the neonatal Fc receptor which is an Fc receptor. Unlike FcγRs which belong to the Immunoglobulin superfamily, human FcRns structurally resemble polypeptides of Major Histocompatibility Complex (MHC) Class I[45]. FcRn is typically expressed as a heterodimer consisting of a transmembrane α or heavy chain in complex with a soluble β or light chain (β2 microglobulin). FcRn shares 22-29% sequence identity with Class I MHC molecules has a non-functional version of the MHC peptide binding groove[46]. Like MHC, the a chain of FcRn consists of three extracellular domains (α1, α2, α3) and a short cytoplasmic tail that anchors the protein to the cell surface. The α1 and α2 domains interact with FcR binding sites in the Fc region of antibodies[47].

In some embodiments, the FcRn targeting moiety is typically a protein or polypeptide that is capable of binding to and mediating uptake of the entire construct by the FcRn receptor. Generally, the FcRn targeting moiety is an Fc of an IgG antibody, preferably of an IgG1 or IgG4 antibody, even more preferably of an IgG1 antibody, or a portion of the Fc that is sufficient to permit binding and uptake of the construct. As used herein, the term "Fc region" includes amino acid sequences derived from the constant region of an antibody heavy chain. The Fc region is the portion of a heavy chain constant region of an antibody beginning at the N-terminal of the hinge region at the papain cleavage site, at about position 216 according to the EU index and including the hinge, CH2, and CH3 domains. Exemplary Fc regions or portions thereof that may be used in the practice of the invention are well known in the art.

In some embodiments, the recombinant chimeric construct of the present invention is a fusion protein that comprises an amino acid sequence consisting of a portion of an Fc region (e.g., the portion of the Fc region that confers binding to FcRn) and an amino acid sequence of a non-immunoglobulin polypeptide that comprises the antigenic portion of the antigen.

As used herein, the term "fusion protein" refers to a chimeric polypeptide which comprises a first amino acid sequence linked to a second amino acid sequence with which it is not naturally linked in nature. As used herein, the terms "linked," "fused" or "fusion" are used interchangeably. These terms refer to the joining together of two or more elements or components, by whatever means including chemical conjugation or recombinant means. An "in-frame" or "operably linked" fusion refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, an in-frame linker sequence. Various detectable labels may be additionally included to facilitate production of the fusion construct or its detection once administered in vivo. In addition, various other functionalities may be included in the constructs. Examples of such functionalities include, but are not limited to, domains of the antigenic protein that are required to exert one or several desired biological activities (e.g. binding to receptor(s) or avoidance of such binding) or that are modified so to increase such biological activities. The fusion protein of the present invention may be produced by any method well known in the art, for example, by chemical synthesis, or by creating and translating a polynucleotide in which the peptide regions are encoded in the desired relationship.

In some embodiments, the Fc region of the fusion protein includes substantially the entire Fc region of an antibody, beginning in the hinge region just upstream of the papain cleavage site which defines IgG Fc chemically (about residue 216 EU numbering, taking the first residue of heavy chain constant region to be 114) and ending at its C-terminus. The precise site at which the fusion is made is not critical; particular sites are well known and may be selected in order to optimize the biological activity, secretion, or binding characteristics of the molecule. Methods for making fusion proteins are known in the art. As used herein, the term "hinge region" includes the portion of a heavy chain molecule that joins the CH1 domain to the CH2 domain, e.g. from about position 216-230 according to the EU number system. This hinge region comprises approximately 25 residues and is flexible, thus allowing the two N-terminal antigen binding regions to move independently. Hinge regions can be subdivided into three distinct domains: upper, middle, and lower hinge domains[48]. As used herein, the term "CH2 domain" includes the portion of a heavy chain molecule that extends, e.g., from about EU positions 231-340. The CH2 domain is unique in that it is not closely paired with another domain. Rather, two N-linked branched carbohydrate chains are interposed between the two CH2 domains of an intact native IgG molecule. As used herein, the term "CH3 domain" includes the portion of a heavy chain molecule that extends approximately 110 residues from N-terminus of the CH2 domain, e.g., from about residue 341-446, EU numbering system). The CH3 domain typically forms the C-terminal portion of the antibody. In some immunoglobulins, however, additional domains may extend from CH3 domain to form the C-terminal portion of the molecule (e.g. the CH4 domain in the chain of IgM and the E chain of IgE).

In some embodiments, the Fc region of the fusion protein does not include the hinge region but comprises the CH2 and CH3 domains that is fused to the amino acid sequence that comprises the antigenic portion of the antigen.

Further methods of reducing the size of the constructs may also be employed, such as those described in US patent applications 2002/0155537, 2007/0014794, and 2010/0254986 (each to Carter et al.), and 2014/0294821 (Dumont et al.). For example, Fc-Fc and antigen-Fc/antigen-Fc dimer formation may be prevented.

In some embodiments, the Fc region may be mutated in order to increase the binding affinity or specificity for the FcRn. Examples of such mutations are summarized in recent reviews[23] and include, but are not limited to, H435A[49], N434A[50] and M428L modifications[51]. FcRn-binding peptides that achieve similar or superior effects as compared to the native Fc domain have also been described[52] and may be used for generating said fusion proteins together with the antigen(s) of interest, further allowing to decrease the relative molecular weight of the added FcRn-binding moiety. In some embodiments, the Fc region may be mutated in order to limit enzymatic degradation, e.g. from pepsin.

In some embodiments, the FcRn-binding moieties are coupled to the surface of nanoparticles, and the antigen(s) of interest are enclosed in such nanoparticles. Examples of nanoparticles include, but are not limited to, biodegradable and biocompatible poly(lactic acid)-bpoly(ethylene glycol) (PLA-PEG) block copolymers[30]. The FcRn-binding moieties can be coupled to the nanoparticle surface by suitable methods, e.g. using ring-opening polymerization with a free terminal maleimide group. This strategy may have the advantage of protecting said antigens from degradation. Procedures to produce suitable nanoparticles are known in the art, examples can be found in[30].

By a "therapeutically effective amount" of the chimeric construct of the present invention as above described is meant a sufficient amount of said construct to reach a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidentally with the specific inhibitor employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

As used herein, the term "mucosal administration" includes any form of administration of the recombinant chimeric construct of the present invention through a mucosal surface that expresses neonatal Fc receptors. The term "mucosal" refers to a tissue comprising a mucous membrane, such as, but not limited to, nasal mucosa, pulmonary mucosa, oral mucosa (including sublingual, oral, buccal, enteral, intestinal, rectal or gastric) or vaginal mucosa. In particular, the term encompasses pulmonary administration and oral administration. In some embodiments, the recombinant chimeric construct of the present invention is delivered via the oral cavity. In some embodiments, the recombinant chimeric construct is delivered via the respiratory tract, e.g. by intranasal delivery, inhalation and any method known in the art.

The recombinant chimeric construct of the present invention is typically administered to the subject in the form of any pharmaceutical composition that is compatible with the mucosal route of administration. For example, the recombinant chimeric construct of the present invention can be administered as a solution or suspension together with a pharmaceutically acceptable carrier. Such a pharmaceutically acceptable carrier can be, for example, water, phosphate buffered saline, normal saline or other physiologically buffered saline, or other solvent or vehicle such as glycol, glycerol, and oil such as olive oil or an injectable organic ester. A pharmaceutically acceptable carrier can also contain liposomes or micelles prepared by mixing the recombinant chimeric construct of the present invention with detergent and a glycoside, such as Quil A. In some embodiments, the recombinant chimeric construct of the present invention is combined with the carrier in any convenient and practical manner, e.g., by solution, suspension, emulsification, admixture, encapsulation, absorption and the like. Such procedures are routine for those skilled in the art. In some embodiments, the recombinant chimeric construct of the present invention is combined or mixed thoroughly with a semi-solid or solid carrier. The mixing can be carried out in any convenient manner such as grinding. Stabilizing agents can also be added in the mixing process in order to protect the composition from loss of therapeutic activity, e.g., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. The composition for oral administration can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the recombinant chimeric construct of the present invention to be released and absorbed by specialized cells, e.g., epithelial enterocytes.

In some embodiments, the chimeric construct may be further protected by degradation by expressing it in biologically contained *Lactococcus lactis* or other suitable bacteria, alone or in combination with immunomodulatory molecules which include, but are not limited to, interleukin-10 and transforming growth factor β. Such formulations may carry the additional advantage of bypassing the need for synthesizing the needed chimeric construct as a recombinant protein of suitable clinical grade and of achieving a steady, low-dose delivery of antigen-Fc constructs that may be more effective at restoring long-term tolerance[53]. This methods are known in the art and examples can be found in[53-55]. Thus the method of the present invention encompasses the use of a recombinant bacteria wherein in the genome of which has been inserted a nucleic acid encoding for the recombinant chimeric construct of the present invention. A recombinant bacteria according to the invention may be selected from the group comprising *Lactobacillus, Leuconostoc, Pediococcus, Lactococcus, Streptococcus, Escherichia, Streptococcus, Agrobacterium, Bacillus, Corynebacterium, Clostridium, Gluconobacter, Citrobacter, Enterobacter, Klebsiella*, and *Pseudomonas*. In some embodiments, a recombinant bacteria according to the invention is a probiotic lactic acid bacteria, in particular of the *Lactococcus* genus, and more particularly of the *Lactococcus lactis* species.

In some embodiments, the chimeric construct of the present invention is administered via the airways, e.g. into the nasal cavity, trachea or lungs. Typically the chimeric construct of the present invention is delivered by any device adapted to introduce a therapeutic composition into the upper and/or lower respiratory tract. In some embodiments, the devices of the present invention may be metered-dose inhalers. The devices may be adapted to deliver the therapeutic compositions of the invention in the form of a finely dispersed mist of liquid, foam or powder. The device may use a piezoelectric effect or ultrasonic vibration to dislodge powder attached on a surface such as a tape in order to generate mist suitable for inhalation. The devices may use any propellant system known to those in the art including, but not limited to, pumps, liquefied gas, compressed gas and the like. Devices typically comprise a container with one or more valves through which the flow of the therapeutic composition travels and an actuator for controlling the flow. In particular, the devices suitable for administering the constructs of the invention include inhalers and nebulisers such as those typically used to deliver steroids to asthmatics. In some cases, where the subject is for example a child, a spacer may be used to facilitate effective administration from the inhaler. Various designs of inhalers are available commercially and may be employed to deliver the medicaments of the invention. These include, without being bound to theory, the Accuhaler, Aerohaler, Aerolizer, Airmax, Akita Jet, Autohaler, Clickhaler, Diskhaler, Easi-breathe inhaler, Fisonair, Integra, Jet inhaler, Miat-haler, Novolizer inhaler, Pari Boy, Pulvinal inhaler, Rotahaler, Spacehaler, Spinhaler, Syncroner inhaler and Turbohaler devices.

The invention will be further illustrated by the following figures and examples. However, these examples and figures should not be interpreted in any way as limiting the scope of the present invention.

FIGURES

FIG. 1. Schematic of the delivery strategy. The physiological pathway that transfers maternal breastmilk IgG to the newborn is exploited. This pathway is FcRn-dependent, and fusion of preproinsulin (PPI) with an IgG Fc fragment grants it access to the bloodstream through the intestinal epithelium.

Figure 2:
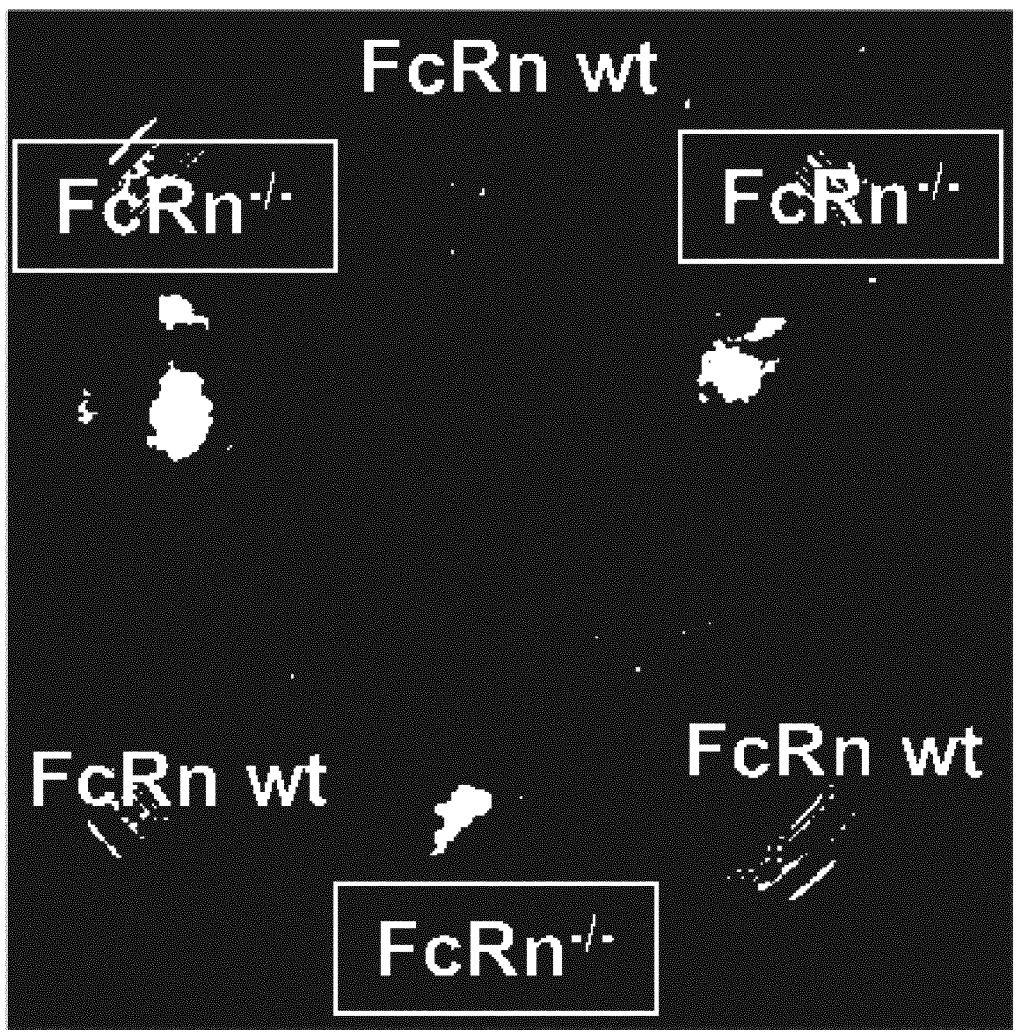

FIG. 2. Orally administered PPI-Fc remains confined to the gut in the absence of FcRn. One-day-old C56BL/6 wild-type (FcRn wt) and FcRn−/− mice were force-fed with 50 μg of Alexa-labeled PPI-Fc and imaged after 72 h. PPI-Fc fluorescence remains detectable in the gut of FcRn−/− but not FcRn wt mice.

Figure 3:
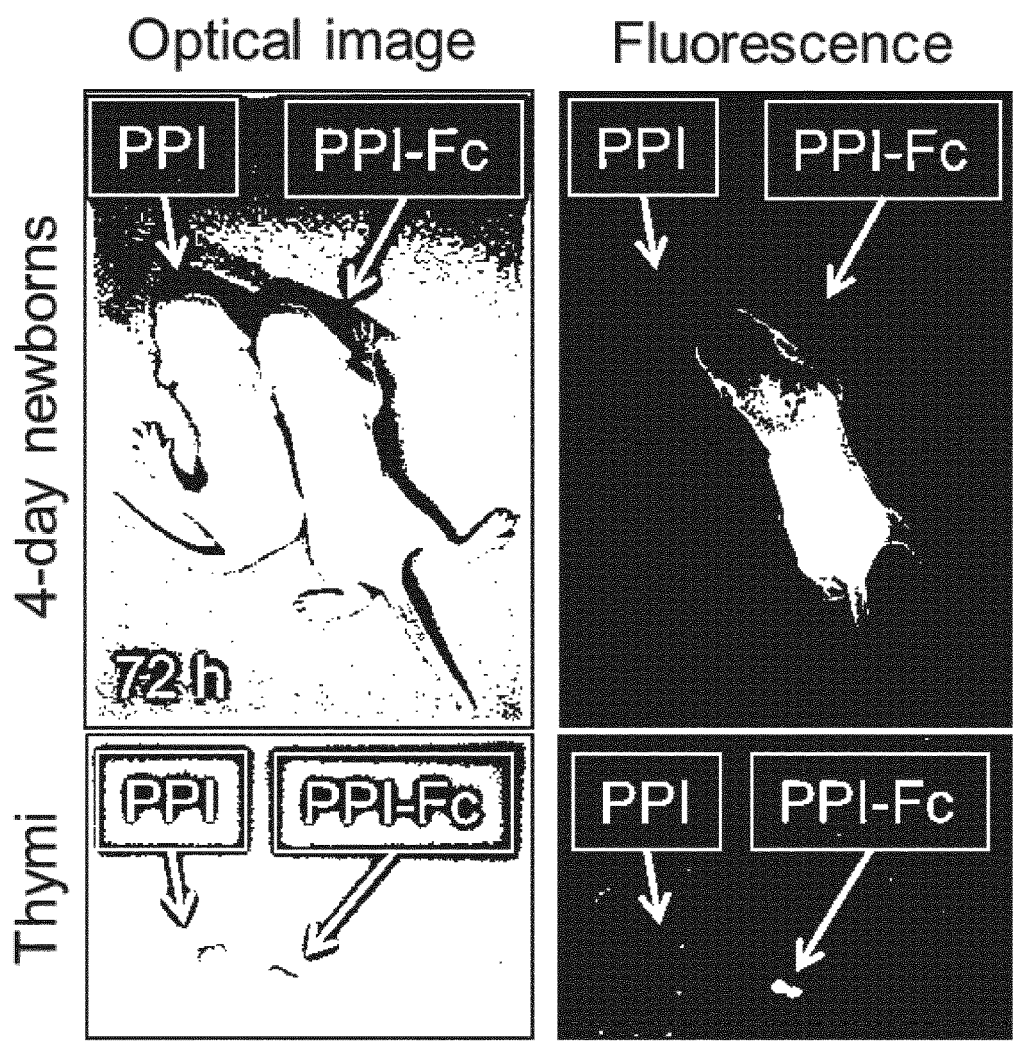

FIG. 3. Systemic and thymic PPI-Fc delivery upon oral administration. One-day-old PPI T-cell receptor (TCR)-transgenic G9C8 NOD newborn mice were force-fed with 50 μg of Alexa-labeled PPI-Fc or PPI and imaged after 72 h. PPI-Fc but not PPI accumulation is detected at the whole body level (top) and in the thymus (bottom). Results refer to a representative experiment out of two performed.

Figure 4:
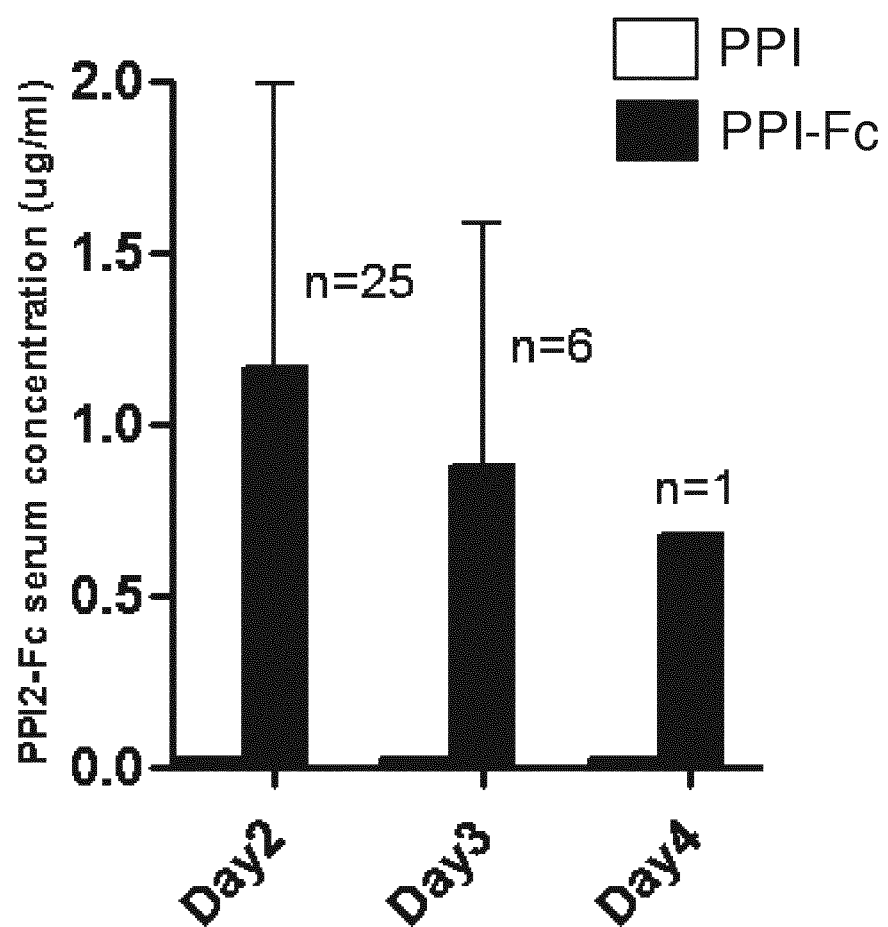

FIG. 4. Serum concentrations of PPI-Fc and PPI upon oral administration. ELISA quantification on serum samples collected at the indicated time points following force-feeding at day 1 as above. Data are depicted as mean+SEM.

FIG. 5. Oral PPI-Fc administration induces immune tolerance. A. Percent spleen $CD8^+CD3^+$ and $CD4^+CD3^+$ T cells in 4-week-old G9C8 mice treated at 1 day of life as above. B. Percent spleen $CD4^+$ T-cell subsets in the same mice. Bars represent median and interquartile ranges. *, $p<0.001$; , $p<0.01$; *, $p<0.05$.

Figure 6:
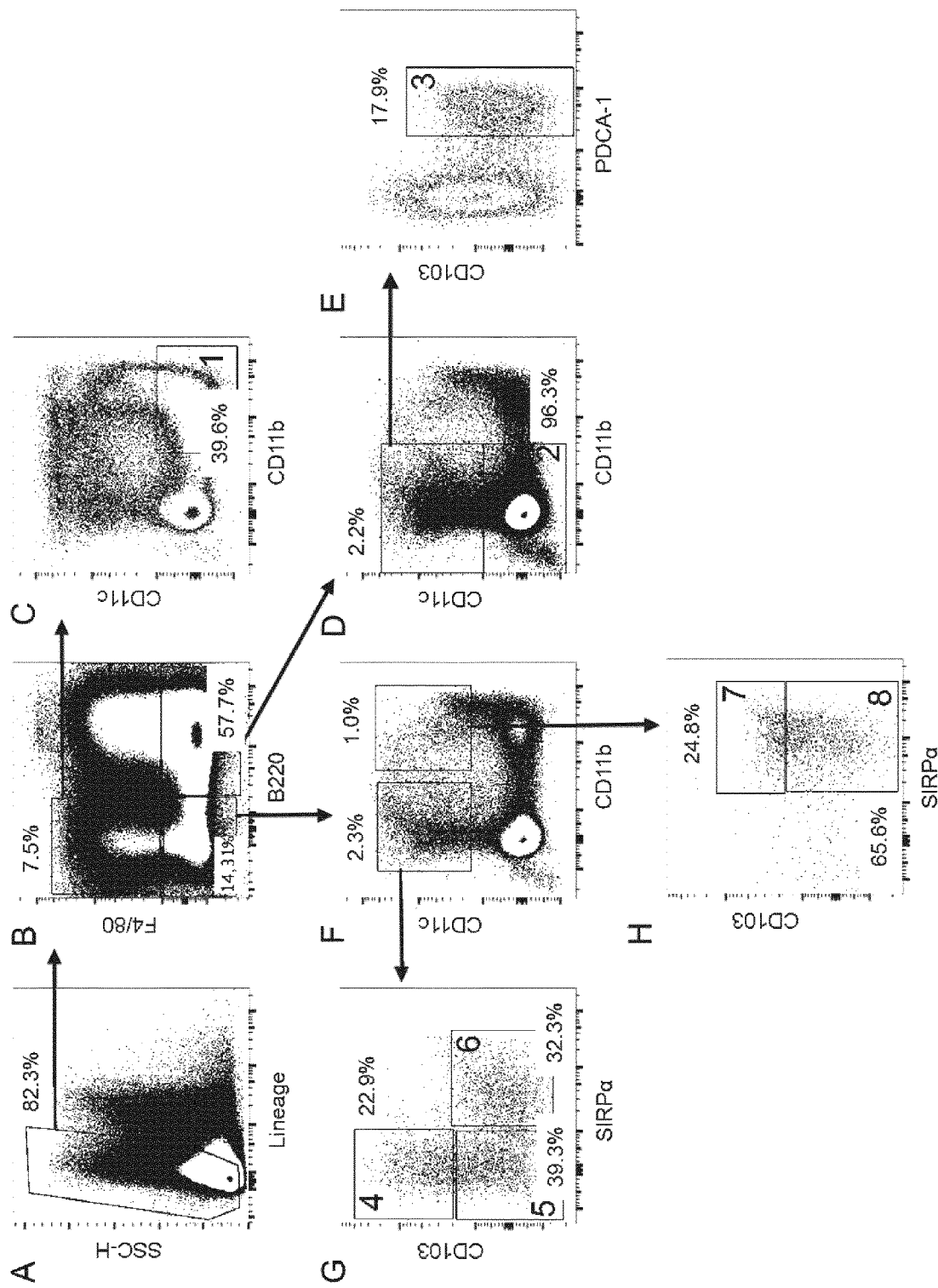

FIG. 6. Gating strategy for the analysis of antigen-presenting cells. Relevant gates are numbered as follows: 1, macrophages; 2, B cells; 3, plasmacytoid dendritic cells (DCs); 4, migratory $CD103^+CD11b^-$ cDCs; 5, resident $CD103^-CD11b^-$ SIRPα$^-$ cDCs; 6, resident $CD103^-CD11b^-$ SIRPα$^+$ cDCs; 7, migratory $CD103^+CD11b^+$ cDCs; 8, resident $CD103^-CD11b^+$ cDCs. Representative results from the spleen of a 2-week-old G9C8 mouse are shown.

Figure 7:
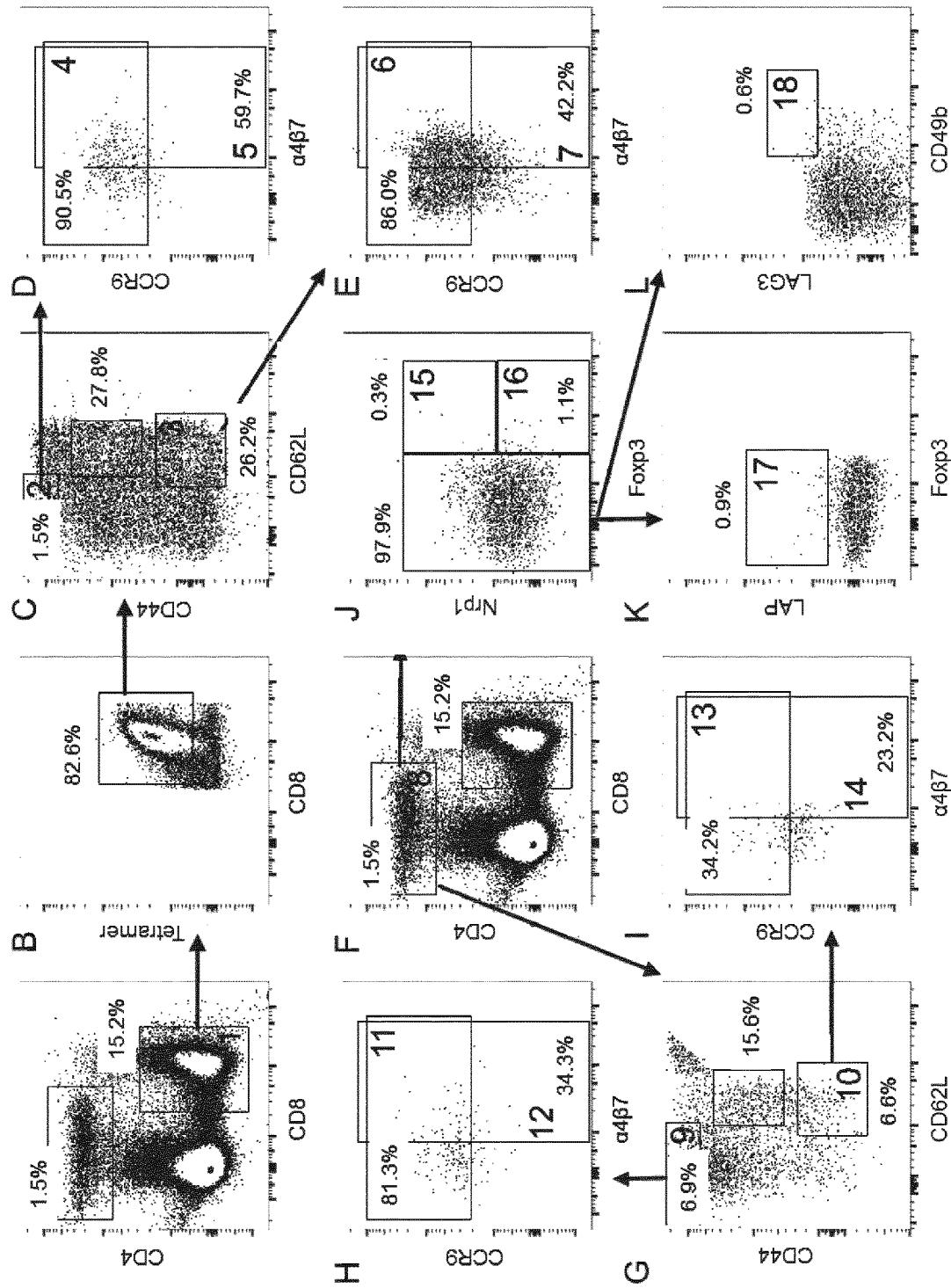

FIG. 7. Gating strategy for the analysis of T-cell subsets. After gating on viable CD3+ cells (not shown), CD8+ (panel A) and CD4+ T cells (panel F) were analysed for the expression of different markers. Relevant gates are numbered as follows: 1, CD8+ T cells; 2, activated/memory CD8+ T cells; 3, naïve CD8+ T cells; 4, CCR9+ activated CD8+ T cells; 5, α4β7+ activated CD8+ T cells; 6, CCR9+ naïve CD8+ T cells; 7, α4β7+ naïve CD8+ T cells; 8, CD4+ T cells; 9, activated/memory CD4+ T cells; 10, naïve CD4+ T cells; 11, CCR9+ activated CD4+ T cells; 12, α4β7+ activated CD4+ T cells; 13, CCR9+ naïve CD4+ T cells; 14, α4β7+ naïve CD4+ T cells; 15, thymic-derived Tregs; 16, peripheral Tregs; 17, Th3 cells; 18, Tr1 cells. Representative results from the spleen of a 2-week-old G9C8 mouse are shown.

Figure 8:
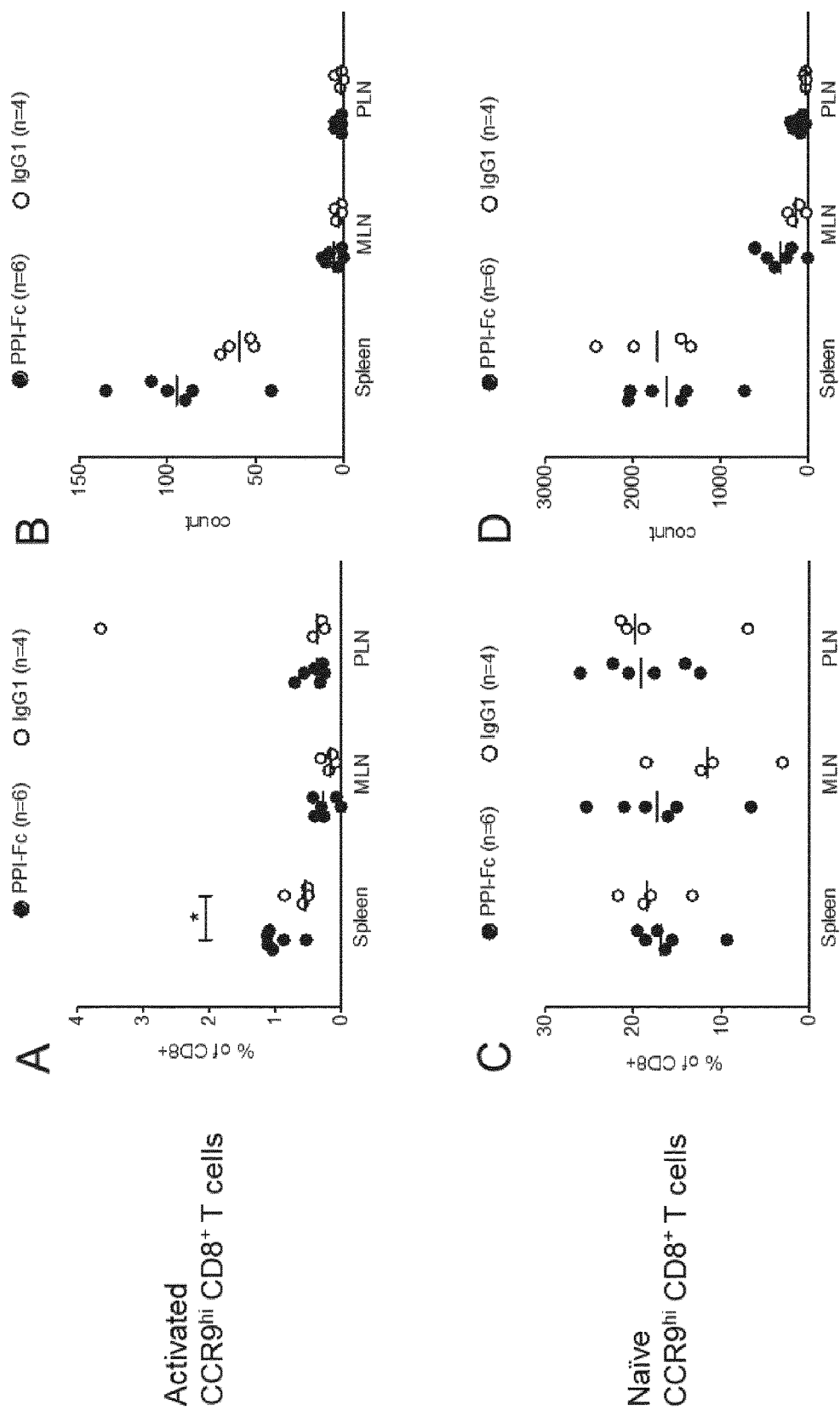

FIG. 8. CCR9$^{hi}$CD8+ T cells in PPI-Fc vs. IgG1-treated G9C8 mice. A-B. Percent (A) and counts (B) of activated (CD44$^{hi}$CD62L−) CCR9$^{hi}$CD8+ T cells in 2-week-old G9C8 mice treated at 1 day of life as above. C-D. Percent (C) and counts (D) of naïve (CD44− CD62L+) CCR9$^{hi}$CD8+ T cells in the same mice. Bars represent medians. *, $p<0.05$.

Figure 9:
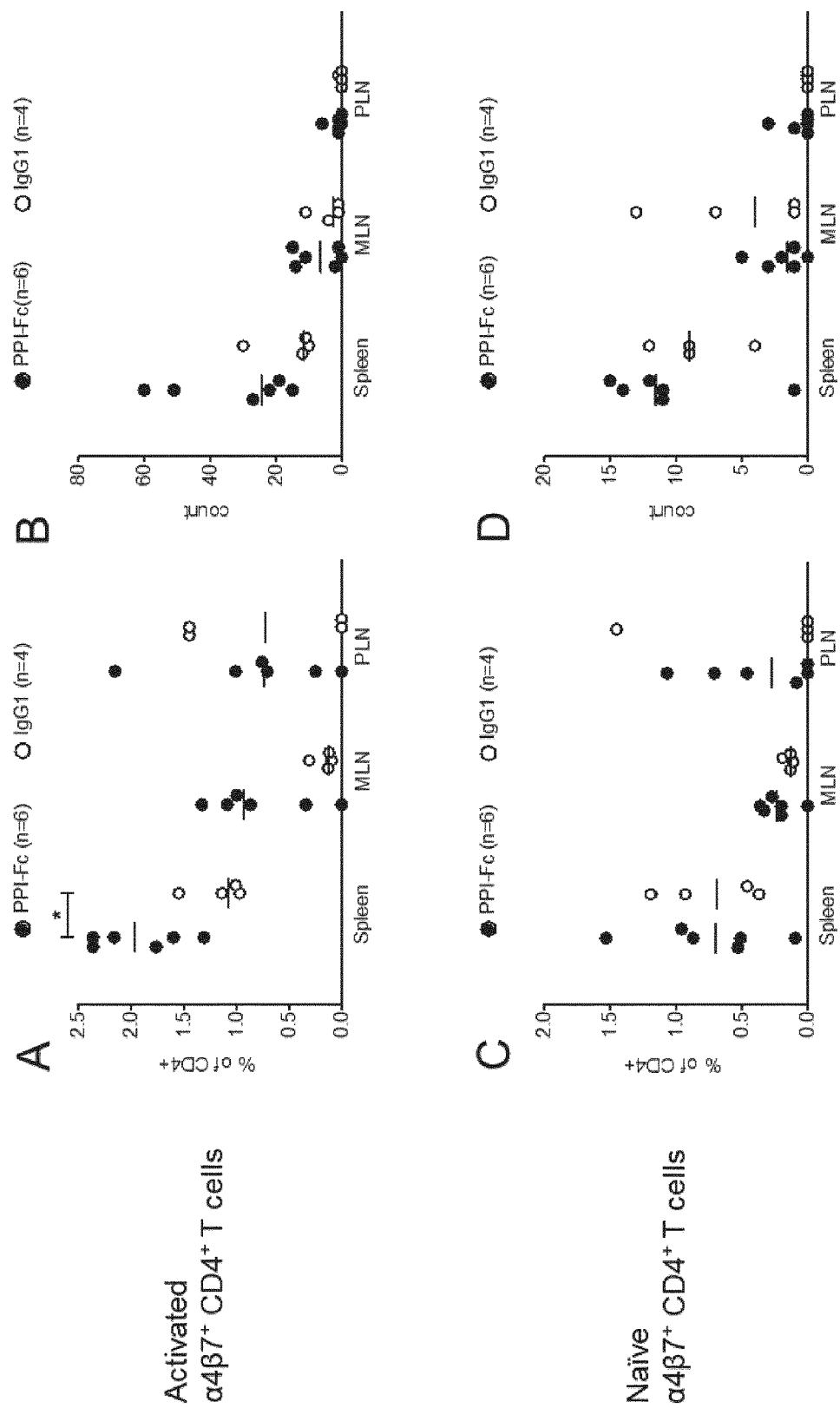

FIG. 9. α4β7+CD4+ T cells in PPI-Fc vs. IgG1-treated G9C8 mice. A-B. Percent (A) and counts (B) of activated (CD44$^{hi}$CD62L−) α4β7+CD4+ T cells in 2-week-old G9C8 mice treated at 1 day of life as above. C-D. Percent (C) and counts (D) of naïve (CD44− CD62L+) α4β7+CD4+ T cells in the same mice. Bars represent medians. *, $p<0.05$.

Figure 10:
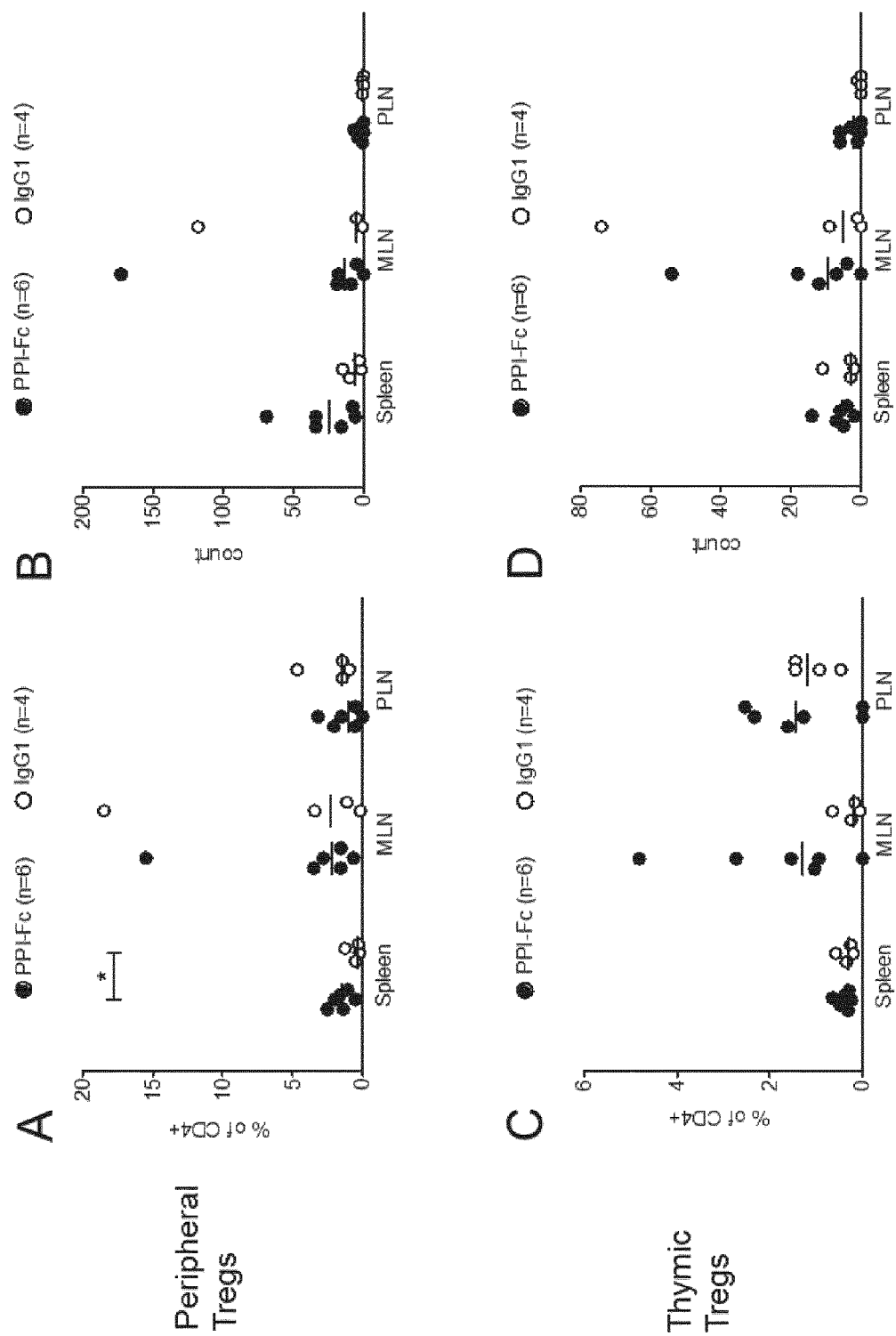

FIG. 10. Peripheral and thymic Tregs in PPI-Fc vs. IgG1-treated G9C8 mice. A-B. Percent (A) and counts (B) of peripheral (NRP1−) Foxp3+CD4+ Tregs in 2-week-old G9C8 mice treated at 1 day of life as above. C-D. Percent (C) and counts (D) of thymic (NRP1+) Foxp3+CD4+ Tregs in the same mice. Bars represent medians. *, $p<0.05$.

Figure 11:
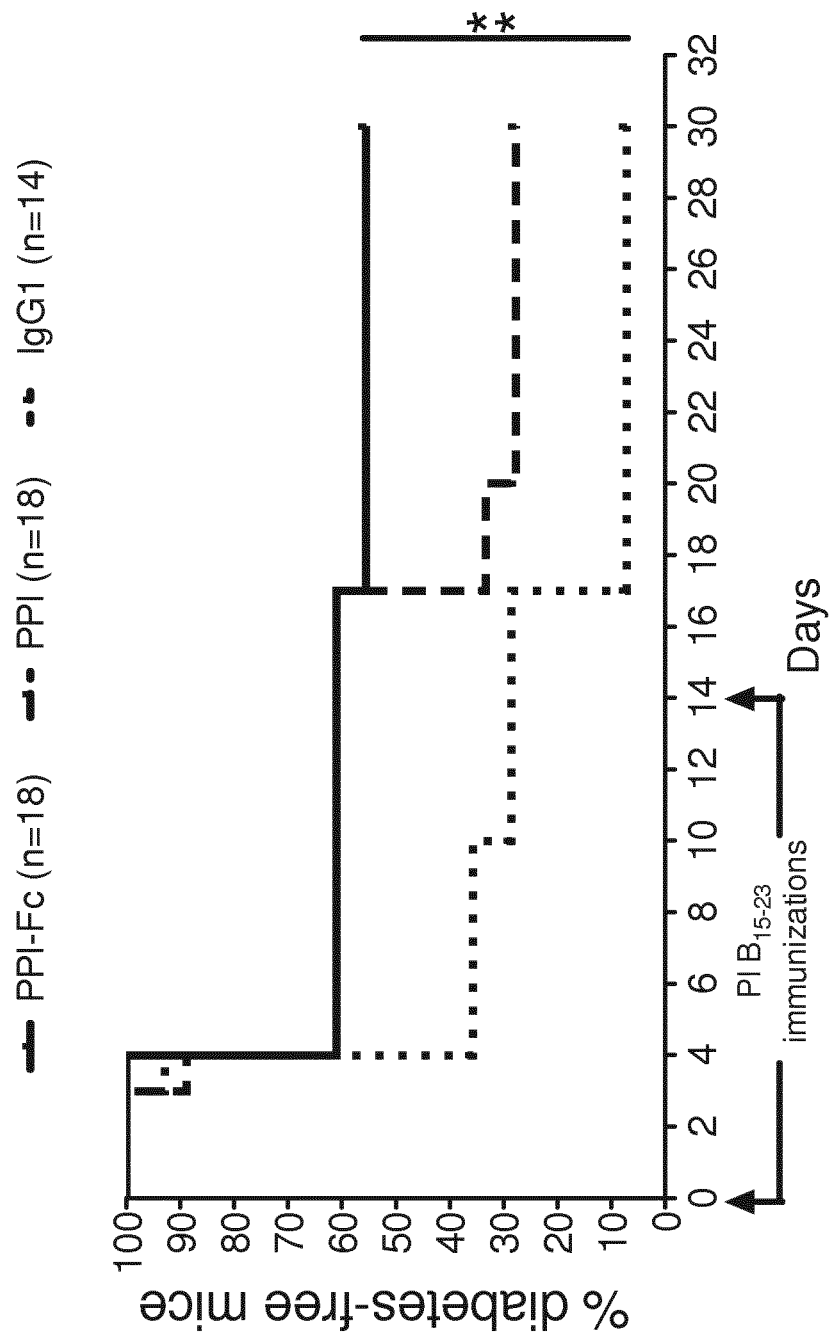

FIG. 11. Orally delivered PPI-Fc protects from diabetes. Diabetes incidence in G9C8 mice force-fed at day 1 with 50 µg PPI-Fc (solid line), equimolar amounts of PPI (dashed line) or IgG1 (dotted line). Diabetes was subsequently induced by immunization with PPIB15-23 and CpG at 4 and 6 weeks of age. **$P<0.01$ by Mann Whitney U test.

EXAMPLE

Material & Methods

Generation of Mouse PPI1-Fc and PPI2-Fc Fusion Proteins

Sequences encoding PPI1 and PPI2 were PCR-amplified from pancreatic and thymic cDNA, respectively, and inserted into pCR4-TOPO plasmids (Invitrogen)[35]. Following digestion with the appropriate restriction enzymes, PPI1/2 sequences were inserted at EcoRV/BglII sites by cohesive end ligation into pFUSE-hIgG1-Fc2 expression vector (InvivoGen), downstream of an IL-2 signal peptide and upstream of the human Fcγ1 sequence. PPI1-Fc and PPI2-Fc sequences were then re-amplified by PCR and ligated at XbaI/XhoI sites into the pFastBac1 expression vector (Invitrogen). These constructs were inserted into the Bac-to-Bac Baculovirus Expression System (Invitrogen), expressed in Hi5 insect cells and protein products purified on Sepharose-coupled protein G (GE Healthcare). Protein identity was confirmed by reducing SDS-PAGE and Western blot using rabbit anti-insulin polyclonal antibody (H-86, Santa Cruz) and mouse anti-human Fc monoclonal Ab (Southern Biotech). PPI1 and PPI2 were purified from Hi5 insect cell pellets as previously described[56]. PPI1-Fc (hereinafter referred to as PPI-Fc) was used in the experiments depicted.

Mice

C56BL/6 wild-type and C56BL/6 FcRn−/− mice were obtained from the Janvier Labs and the Jackson Laboratory, respectively. G9C8 Cα−/− NOD mice are transgenic for a PPI$_{B15-23}$ TCR and have been previously described and characterized[35,37].

In Vivo PPI-Fc Imaging

PPI-Fc and PPI proteins were conjugated with Alexa Fluor (AF) 680 using SAIVI Rapid Antibody/Protein labeling kit (Invitrogen). One-day-old newborn mice were force-fed with 50 µg PPI-Fc or equimolar amounts of PPI. Fluorescence was detected using the Fluobeam imaging system (Fluoptics) at a 690 nm excitation and >700 nm emission wavelengths, with 50-100 ms exposures.

ELISA Quantification of Serum PPI-Fc and PPI Concentrations

Following force-feeding as above, blood was collected at the indicated time points for ELISA quantification, with standard curves obtained by sequential dilutions of PPI-Fc and PPI proteins. Both PPI-Fc and PPI were captured with plate-coated H-86 anti-insulin Ab (Santa Cruz). PPI-Fc was detected with a horseradish peroxidase-labeled goat anti-human Fc antibody (Southern Biotech). PPI was revealed with an anti-proinsulin monoclonal Ab (KL-1; kindly provided by Dr. L. Harrison, Walter and Eliza Hall Institute, Parkville, Australia).

Spleen T-cell Phenotyping

The following monoclonal antibodies were used on splenocytes retrieved from treated mice: PE-labeled anti-Foxp3, APC-eFluor780-labeled anti-CD3ε (eBioscience); APC-labeled anti-neuropilin-1 (NRP1; R&D); Brilliant Violet (BV) 605-labeled anti-CD4 and BV711-labeled anti-CD8a (BioLegend). Cells were additionally stained with Live/Dead Red (Invitrogen).

$K^d$ Multimer Preparation

Monomers composed of the mouse MHC class I heavy chain H-2Kd, human β2-microglobulin and the PPI B15-23 peptide (LYLVCGERL) were synthesized as described[35] and incubated with BV650-coupled streptavidin (mole:mole ratio 4:1) for 1 h. D-biotin and bovine serum albumin were then added at 25 µM and 0.5% concentrations, respectively. The obtained multimers (MMrs) were stored at 4° C. protected from light and used the same day.

Phenotyping of subsets of antigen-presenting cells and T cells in the spleen and lymph nodes.

All cells were washed and resuspended in PBS 1× prior to transfer into 96-well V-bottom plated (200 µl/well) for FACS staining. BD CompBeads (10 µl/well, 1 drop in 500 µl PBS) were added to each well prior to staining to normalize cell counts. Two antibody panels were used, as follows.

T-cell panel. Dasatinib (50 µM, 100 µl/well) was added to each cell pellet for 30 min at 37° C. After centrifugation, cells were resuspended in 18 µl of MMr solution containing a 20% dilution of 50 µM dasatinib for 20 min at room temperature, followed by incubation for 20 min at 4° C. with 18 µL of the following antibody premix: Live/DEAD Aqua (Invitrogen, 1/1,000), CD3-APC-eFluor780 (clone 145-2C11, eBioscience, 1/100), CD4-BV711 (clone RM4-5, BD Biosciences, 1/200), CD8-AF700 (clone 53-6.7, BD Biosciences, 1/150), CCR9-PE-Cy7 (clone CW-1.2, BioLegend, 1/100); NRP1-APC (clone 3E12, BioLegend, 1/50), LPAM-1 (α4β7)-PE-CF594 (clone ATK32, BD Biosciences, 1/100), latency-associated peptide (LAP)-BV421 (clone TW7-16B4, BioLegend, 1/200), CD62L-BV605 (clone MEL-14, BD Biosciences, 1/200), CD44-BV786 (clone IM7, BD Biosciences, 1/100). A second 10 µL antibody mix was then added for 15 min at 37° C.: CD49b-FITC (clone HMα2, BioLegend, 1/200), LAG3-PerCP-Cy5.5 (clone C9B7W, BD Biosciences, 1/200). Cells were then washed in PBS, fixed and permeabilised with the Foxp3 Fix/Perm Buffer Set (BioLegend), and incubated with 30 µl anti-Foxp3 antibody (Foxp3-PE, clone FJK-16s, eBioscience, 1/50 in FoxP3/Perm buffer). After a final wash, cells were resuspended in 200 µl PBS 1× and kept at 4° C. prior to flow cytometry acquisition.

Antigen presenting cell (APC) panel. An identical staining protocol was applied without fixation and permeabilisation, with an incubation for 20 min at 4° C. with 30 µl of the following antibody mix: Live/DEAD Aqua (Invitrogen, 1/1,000), NK1.1-BV510 (clone PK136, BD Biosciences, 1/100), CD3-BV510 (clone 145-2C11, BD Biosciences, 1/100), F4/80-BV711 (clone BM8, BioLegend, 1/50), CD8-AF700 (clone 53-6.7, BD Biosciences, 1/150), B220-PE-Cy7 (clone RA3-6B2, BD Biosciences, 1/150), SIRPα-PerCP-eF1710 (clone P84, eBioscience, 1/50), PDCA-1-Pacific Blue (clone 927, BioLegend, 1/200), CD11b-BV650 (clone M1/70, BD Biosciences, 1/150), CD11c-BV605 (clone N418, BioLegend, 1/50), CD103-BV786 (clone M290, BD Biosciences, 1/100).

PPI-Fc Treatment, Diabetes Induction and Follow-up

G9Cα−/−.NOD mice were force-fed on day 1 after birth with 50 µg PPI-Fc or control proteins, namely equimolar quantities of Fc-devoid PPI or Herceptin IgG1. For diabetes induction, 4-week-old mice were primed with 50 µg $PPI_{B15-23}$ peptide and 100 µg CpG 4 days after weaning, followed by a second identical immunization 15 days later. Diabetes development was monitored by testing glycosuria and confirmed by glycaemia when positive. Diabetic mice were sacrificed by cervical dislocation.

Results

The Intestinal Transfer of Orally Administered PPI-Fc is FcRn- and Fc-dependent

A schematic of the strategy used is depicted in FIG. 1. We exploited the intestinal FcRn pathway that physiologically delivers breastmilk IgG to the newborn. To this end, we fused the PPI1 or PPI2 protein with the N-terminus of the CH2-CH3 Fc domain from human IgG1 to obtain PPI1-Fc and PPI2-Fc fusion proteins. While Fc-devoid PPI1/2 is not able to cross the intestinal epithelium, addition of the Fc moiety should favor this transfer. We explored this strategy using a PPI1-Fc construct (hereinafter referred to as PPI-Fc).

We first performed ex vivo imaging on 1-day-old FcRn−/− and wild-type C56BL/6 mice force-fed with fluorescently labeled PPI1-Fc and sacrificed after 72 h (FIG. 2). The PPI-Fc fluorescence was still detectable in the intestines of FcRn−/− but not of wild-type mice, suggesting lack of transfer in the absence of FcRn.

To verify the occurrence of such transfer, 1-day-old G9C8 newborn mice were force-fed with fluorescently labeled PPI-Fc or Fc-devoid PPI (FIG. 3). After 72 h, systemic PPI-Fc accumulation was promptly visualized, which was not the case for PPI. PPI-Fc, but not PPI, was also visualized in the thymus.

Serum PPI1-Fc concentrations (FIG. 4) were of ~1 µg/ml at 24 h after administration (day 2) and remained relatively stable up to 72 h after (day 3; ~0.75 µg/ml). PPI1 was not detected at any of these time points.

Collectively, these results show that oral administration of a single 50 µg dose of PPI-Fc, but not of PPI, results in intestinal transfer, systemic antigen bioavailability and delivery to the thymus, which is FcRn- and Fc-dependent.

Oral PPI-Fc vaccination induces tolerogenic T-cell modifications.

Figure 5A:
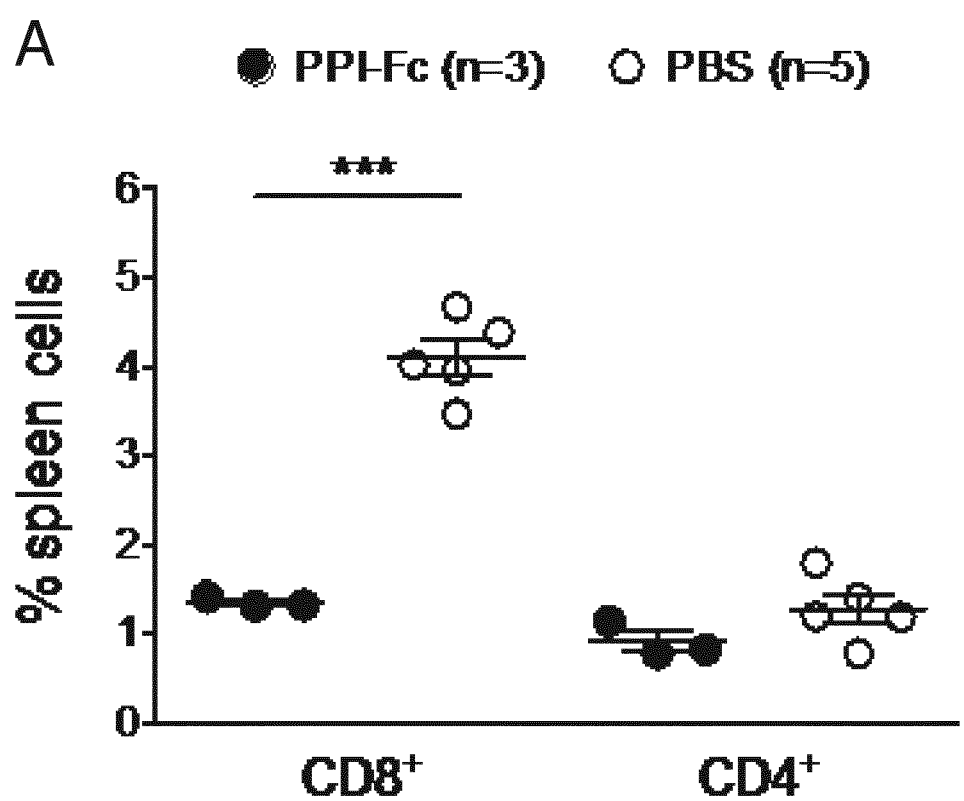
Figure 5B:
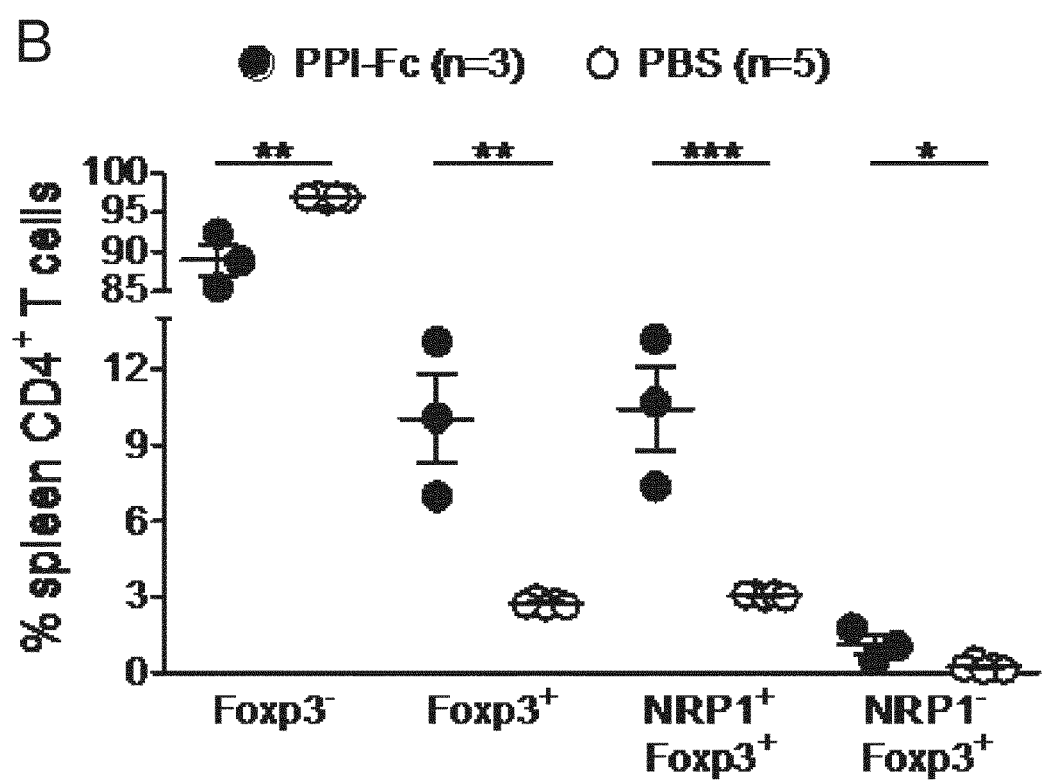

We next assessed whether thymic PPI-Fc delivery induced T-cell modifications compatible with immune tolerance (FIG. 5A). Splenocytes obtained at 4 weeks of age following treatment at day 1 of life as above displayed significantly decreased numbers of $CD8^+$ effector T cells in PPI-Fc-treated newborns compared with PBS-treated ones. No significant difference was highlighted in the number of total $CD4^+$ T cells between PPI-Fc- and PBS-treated mice. However, when analyzing $CD4^+$ T cell subsets, significant differences were detected (FIG. 5B). Compared with PBS-treated mice, PPI1-Fc-treated animals displayed decreased numbers of $CD4^+$ effector T cells (Foxp3−) and increased numbers of $Foxp3^+$ regulatory T cells (Tregs), both thymic-derived ($NRP1/CD304^+$) and peripherally induced (NRP1/CD304−).

A second set of experiments was performed by comparing G9C8 mice force fed with either PPI-Fc or IgG1, in order to differentiate the effects induced by the Fc moiety by those relying on the PPI antigenic portion. These mice were analyzed at 2 weeks of age, i.e. closer to the first day of life at which they were orally vaccinated. Both APC and T-cell subsets were analyzed in the spleen, mesenteric lymph nodes (MLNs) and pancreatic lymph nodes (PLNs).

The APC gating strategy is depicted in FIG. 6. After gating on forward and side scatter and live cells (not shown), CD3−NK1.1− (lineage-negative) cells were selected to exclude T and NK cells, respectively (FIG. 6A). Three gates were then selected according to two markers: $F4/80^+B220^-$, $F4/80^-B220^+$ and $F4/80^-B220^-$ (FIG. 6B). $F4/80^+B220^-$ cells were then plotted for CD11c and CD11b expression to identify $CD11c^-CD11b^+$ macrophages (FIG. 6C, gate 1). Similarly, $F4/80^-B220^+$ cells were plotted for CD11c and CD11b markers to gate $CD11c^-CD11b^-$ B cells (FIG. 6D, gate 2) and $CD11b^-CD11c^+$ cells, which reveal the plasmacytoid dendritic cell (pDC) population upon further gating for PDCA-1 marker (FIG. 6E, gate 3) and for the migration marker CD103. Among $F4/80^-B220^-$ cells, two gates were selected according to CD11c and CD11b markers (FIG. 6F). Collectively, these $CD11c^+$ fractions correspond to conventional dendritic cells (cDCs), which are further divided in CD11b− cDCs, either migratory ($CD103^+$, gate 4) or resident (CD103−, gate 5, FIG. 6G); and $CD11b^+$ cDCs, again either migratory ($CD103^+$, gate 7) or resident (CD103−, gate 8, FIG. 6H). An additional population of $CD103^-SIRPα^+$ CD11b− cDCs not detailed in the literature was also visualized (gate 6, FIG. 6G). When comparing PPI-Fc- and IgG1-fed 2-week-old mice, no differences were highlighted in the frequency or counts of these different APC populations (not shown). Collectively, these results show that APC composition is not influenced by prior oral vaccination, at least at the 2-week time point analyzed.

The T-cell gating strategy is depicted in FIG. 7. Among lineage−$CD3^+$ cells, $CD8^+$ T cells were gated (FIG. 7A, gate 1). Among $CD8^+$ cells, $MMr^+$ cells were selected to verify their specificity for the $PPI_{B15-23}$ peptide (FIG. 7B). $CD8^+$ T cells were further gated for CD44 and CD62L. While the $CD44^{hi}CD62L^-$ subset corresponds to activated/memory $CD8^+$ T cells (gate 2), $CD44^-CD62L^+$ are naïve cells (gate 3, FIG. 7C). Finally, both activated and naïve $CD8^+$ T cells were analysed for the expression of the gut-homing markers CCR9 and α4β7 (gates 4-5, FIG. 7D; and gates 6-7, FIG. 7E). For $CD4^+$ T cells (FIG. 7F), the same phenotypic markers (CD44 and CD62L, FIG. 7G; and CCR9 and α4β7, FIG. 7H-I) were used. In addition, three Treg populations were analysed: classical Tregs, either thymic-derived ($Foxp3^+NPR1^+$; gate 15) or peripherally induced ($Foxp3^+$ NRP1−; gate 16, FIG. 7J); T helper (Th)3 cells ($LAP^+$ FoxP3−; gate 17, FIG. 7K) and T regulatory 1 (Tr1) cells ($Foxp3^-CD49b^+LAG3^+$; gate 18, FIG. 7L). Using this gating strategy, few differences between PPI-Fc- and IgG1-fed animals were already visible at 2 weeks of age. First, the proportion of splenic CCR9$^{hi}$CD8$^+$ T cells, which are likely to originate in the gut, was increased in PPI-Fc-fed mice (FIG. 8). Such increase was confined to activated CCR9$^{hi}$CD8$^+$ T cells (FIG. 8A-B) and was not observed in the naïve CD8$^+$ subset (FIG. 8C-D), further suggesting that T cells migrate to the spleen from the gut upon encounter with their PPI B15-23 cognate antigen that is recognized by most T cells in this G9C8 TCR-transgenic model. Second, a similar increase in the PPI-Fc group was observed for splenic α4β7$^+$CD4$^+$ T cells (FIG. 9), another population reported to originate in the gut. Also in this case, this increase was observed only in the activated (FIG. 9A-B) but not in the naïve subset of these cells (FIG. 9C-D), likely reflecting prior cognate PPI-Fc priming in the gut. Third, a minor increase in splenic peripheral Tregs was observed with the PPI-Fc treatment (FIG. 10A-B), while splenic thymus-derived Tregs were not increased at this time point (FIG. 10C-D).

Collectively, these results show that oral PPI-Fc vaccination induces T-cell modifications characteristic of oral tolerance, namely an increase in gut-derived activated CD8$^+$ and CD4$^+$ T cells and in peripheral Tregs at 2 weeks of age; and modifications suggestive of deletional and regulatory tolerance mechanisms, namely decreased CD8$^+$ and CD4$^+$ effector T cells and increased CD4$^+$ Tregs at 4 weeks. Of further note, the proposed mechanism of action for oral PPI-Fc vaccination is different than for classical oral tolerance with Fc-devoid antigens. Systemic and thymic antigen-Fc bioavailability is here achieved, boosting both peripheral and central tolerance mechanisms, as evidenced by the increased numbers of both thymic- and peripheral-derived Tregs.

Neonatal Oral PPI-Fc Vaccination Protects G9C8 Mice from Diabetes Development

Finally, we verified whether PPI-Fc oral vaccination and the associated T-cell modifications resulted in diabetes protection later in life. To this end, 1-day-old newborn G9C8 mice were orally vaccinated with 50 µg PPI-Fc. At 4 and 6 weeks of age, they were then immunized with PPI B15-23 peptide and CpG to induce diabetes and prospectively followed. For controls, equimolar amounts of recombinant IgG1 (i.e., irrelevant protein with preserved FcRn binding) and PPI (i.e., cognate antigen with no FcRn binding) were administered. In IgG1-fed mice, diabetes development was rapid and synchronous with prime-boost immunizations, affecting 93% of mice. Conversely, only 44% of mice developed diabetes when fed with PPI-Fc (p<0.01). As expected, PPI gave an intermediate protection, with 72% of mice ultimately developing diabetes. Collectively, these results demonstrate that oral vaccination with PPI-Fc protects G9C8 mice from diabetes more efficiently than Fc-devoid PPI.

REFERENCES

Throughout this application, various references describe the state of the art to which this invention pertains. The disclosures of these references are hereby incorporated by reference into the present disclosure.

1. Culina S, Boitard C, Mallone R. Antigen-based immune therapeutics for type 1 diabetes: magic bullets or ordinary blanks? *Clin Dev Immunol.* 2011; 2011:286248.
2. Brezar V, Carel J C, Boitard C, Mallone R. Beyond the hormone: insulin as an autoimmune target in type 1 diabetes. *Endocr Rev.* 2011; 32:623-669.
3. Diabetes Prevention Trial-Type 1 Diabetes Study G. Effects of insulin in relatives of patients with type 1 diabetes mellitus. *N Engl J Med.* 2002; 346:1685-1691.
4. Ludvigsson J, Krisky D, Casas R, Battelino T, Castano L, Greening J, Kordonouri O, Otonkoski T, Pozzilli P, Robert J J, Veeze H J, Palmer J. GAD65 antigen therapy in recently diagnosed type 1 diabetes mellitus. *N Engl J Med.* 2012; 366:433-442.
5. Nakayama M, Abiru N, Moriyama H, Babaya N, Liu E, Miao D, Yu L, Wegmann D R, Hutton J C, Elliott J F, Eisenbarth G S. Prime role for an insulin epitope in the development of type 1 diabetes in NOD mice. *Nature.* 2005; 435:220-223.
6. Krishnamurthy B, Dudek N L, McKenzie M D, Purcell A W, Brooks A G, Gellert S, Colman P G, Harrison L C, Lew A M, Thomas H E, Kay T W. Responses against islet antigens in NOD mice are prevented by tolerance to proinsulin but not IGRP. *J Clin Invest.* 2006; 116:3258-3265.
7. Fourlanos S, Perry C, Gellert S A, Martinuzzi E, Mallone R, Butler J, Colman P G, Harrison L C. Evidence that nasal insulin induces immune tolerance to insulin in adults with autoimmune diabetes. *Diabetes.* 2011; 60:1237-1245.
8. Mallone R, Roep B O. Biomarkers for immune intervention trials in type 1 diabetes. *Clin Immunol.* 2013; 149:286-296.
9. Culina S, Mallone R. Immune biomarkers in immunotherapeutic trials for type 1 diabetes: Cui prodest? *Diabetes Metab.* 2012; 38:379-385.
10. Parikka V, Nanto-Salonen K, Saarinen M, Simell T, Ilonen J, Hyoty H, Veijola R, Knip M, Simell O. Early seroconversion and rapidly increasing autoantibody concentrations predict prepubertal manifestation of type 1 diabetes in children at genetic risk. *Diabetologia.* 2012; 55:1926-1936.
11. Ziegler A G, Bonifacio E, Group B-BS. Age-related islet autoantibody incidence in offspring of patients with type 1 diabetes. *Diabetologia.* 2012; 55:1937-1943.
12. Achenbach P, Barker J, Bonifacio E. Modulating the natural history of type 1 diabetes in children at high genetic risk by mucosal insulin immunization. *Curr Diab Rep.* 2008; 8:87-93.
13. Bonifacio E, Ziegler A G, Klingensmith G, Schober E, Bingley P J, Rottenkolber M, Theil A, Eugster A, Puff R, Peplow C, Buettner F, Lange K, Hasford J, Achenbach P, Group P-PS. Effects of high-dose oral insulin on immune responses in children at high risk for type 1 diabetes: the Pre-POINT randomized clinical trial. *JAMA.* 2015; 313:1541-1549.
14. Mold J E, Michaelsson J, Burt T D, Muench M O, Beckerman K P, Busch M P, Lee T H, Nixon D F, McCune J M. Maternal alloantigens promote the development of tolerogenic fetal regulatory T cells in utero. *Science.* 2008; 322:1562-1565.
15. Guerau-de-Arellano M, Martinic M, Benoist C, Mathis D. Neonatal tolerance revisited: a perinatal window for Aire control of autoimmunity. *J Exp Med.* 2009; 206:1245-1252.
16. Billingham R E, Brent L, Medawar P B. Actively acquired tolerance of foreign cells. *Nature.* 1953; 172:603-606.
17. Klein L, Kyewski B, Allen P M, Hogquist K A. Positive and negative selection of the T cell repertoire: what thymocytes see (and don't see). *Nat Rev Immunol.* 2014; 14:377-391.
18. Thebault-Baumont K, Dubois-Laforgue D, Krief P, Briand J P, Halbout P, Vallon-Geoffroy K, Morin J, Laloux V, Lehuen A, Carel J C, Jami J, Muller S, Boitard C. Acceleration of type 1 diabetes mellitus in proinsulin 2-deficient NOD mice. *J Clin Invest.* 2003; 111:851-857.

19. Faideau B, Lotton C, Lucas B, Tardivel I, Elliott J F, Boitard C, Carel J C. Tolerance to proinsulin-2 is due to radioresistant thymic cells. *J Immunol.* 2006; 177:53-60.

20. Pugliese A, Zeller M, Fernandez A, Jr., Zalcberg L J, Bartlett R J, Ricordi C, Pietropaolo M, Eisenbarth G S, Bennett S T, Patel D D. The insulin gene is transcribed in the human thymus and transcription levels correlated with allelic variation at the INS VNTR-IDDM2 susceptibility locus for type 1 diabetes. *Nat Genet.* 1997; 15:293-297.

21. Roopenian D C, Akilesh S. FcRn: the neonatal Fc receptor comes of age. *Nat Rev Immunol.* 2007; 7:715-725.

22. Huber A H, Kelley R F, Gastinel L N, Bjorkman P J. Crystallization and stoichiometry of binding of a complex between a rat intestinal Fc receptor and Fc. *J Mol Biol.* 1993; 230:1077-1083.

23. Kuo T T, Aveson V G. Neonatal Fc receptor and IgG-based therapeutics. *MAbs.* 2011; 3:422-430.

24. Zhu X, Meng G, Dickinson B L, Li X, Mizoguchi E, Miao L, Wang Y, Robert C, Wu B, Smith P D, Lencer W I, Blumberg R S. MHC class I-related neonatal Fc receptor for IgG is functionally expressed in monocytes, intestinal macrophages, and dendritic cells. *J Immunol.* 2001; 166:3266-3276.

25. Israel E J, Taylor S, Wu Z, Mizoguchi E, Blumberg R S, Bhan A, Simister N E. Expression of the neonatal Fc receptor, FcRn, on human intestinal epithelial cells. *Immunology.* 1997; 92:69-74.

26. Dickinson B L, Badizadegan K, Wu Z, Ahouse J C, Zhu X, Simister N E, Blumberg R S, Lencer W I. Bidirectional FcRn-dependent IgG transport in a polarized human intestinal epithelial cell line. *J Clin Invest.* 1999; 104:903-911.

27. Hornby P J, Cooper P R, Kliwinski C, Ragwan E, Mabus J R, Harman B, Thompson S, Kauffman A L, Yan Z, Tam S H, Dorai H, Powers G D, Giles-Komar J. Human and non-human primate intestinal FcRn expression and immunoglobulin G transcytosis. *Pharm Res.* 2014; 31:908-922.

28. Yoshida M, Claypool S M, Wagner J S, Mizoguchi E, Mizoguchi A, Roopenian D C, Lencer W I, Blumberg R S. Human neonatal Fc receptor mediates transport of IgG into luminal secretions for delivery of antigens to mucosal dendritic cells. *Immunity.* 2004; 20:769-783.

29. Low S C, Nunes S L, Bitonti A J, Dumont J A. Oral and pulmonary delivery of FSH-Fc fusion proteins via neonatal Fc receptor-mediated transcytosis. *Hum Reprod.* 2005; 20:1805-1813.

30. Pridgen E M, Alexis F, Kuo T T, Levy-Nissenbaum E, Karnik R, Blumberg R S, Langer R, Farokhzad O C. Transepithelial transport of Fc-targeted nanoparticles by the neonatal fc receptor for oral delivery. *Sci Transl Med.* 2013; 5:213ra167.

31. Spiekermann G M, Finn P W, Ward E S, Dumont J, Dickinson B L, Blumberg R S, Lencer W I. Receptor-mediated immunoglobulin G transport across mucosal barriers in adult life: functional expression of FcRn in the mammalian lung. *J Exp Med.* 2002; 196:303-310.

32. Bitonti A J, Dumont J A, Low S C, Peters R T, Kropp K E, Palombella V J, Stattel J M, Lu Y, Tan C A, Song J J, Garcia A M, Simister N E, Spiekermann G M, Lencer W I, Blumberg R S. Pulmonary delivery of an erythropoietin Fc fusion protein in non-human primates through an immunoglobulin transport pathway. *Proc Natl Acad Sci USA.* 2004; 101:9763-9768.

33. Dumont J A, Bitonti A J, Clark D, Evans S, Pickford M, Newman S P. Delivery of an erythropoietin-Fc fusion protein by inhalation in humans through an immunoglobulin transport pathway. *J Aerosol Med.* 2005; 18:294-303.

34. Gupta N, Culina S, Meslier Y, Dimitrov J, Arnoult C, Delignat S, Gangadharan B, Lecerf M, Justesen S, Gouilleux-Gruart V, Salomon B L, Scott D W, Kaveri S V, Mallone R, Lacroix-Desmazes S. Regulation of immune responses to antigens and protein therapeutics by transplacental induction of central and peripheral T-cell tolerance. *Sci Transl Med.* 2015; 7:275ra221.

35. Culina S, Gupta N, Boisgard R, Afonso G, Gagnerault M C, Dimitrov J, Osterbye T, Justesen S, Luce S, Attias M, Kyewski B, Buus S, Wong F S, Lacroix-Desmazes S, Mallone R. Materno-fetal transfer of preproinsulin through the neonatal Fc receptor protects from autoimmune diabetes. *Diabetes.* 2015; in press.

36. Narendran P. An alternative approach to immunomodulation for type 1 diabetes: antigen specific immunotherapy in utero. *Diabetes.* 2015; in press.

37. Wong F S, Siew L K, Scott G, Thomas I J, Chapman S, Viret C, Wen L. Activation of insulin-reactive CD8 T cells for development of autoimmune diabetes. *Diabetes.* 2009; 58:1156-1164.

38. Hong S, Wilson M T, Serizawa I, Wu L, Singh N, Naidenko O V, Miura T, Haba T, Scherer D C, Wei J, Kronenberg M, Koezuka Y, Van K L. The natural killer T-cell ligand alpha-galactosylceramide prevents autoimmune diabetes in non-obese diabetic mice. *NatMed.* 2001; 7:1052-1056.

39. Lehuen A, Diana J, Zaccone P, Cooke A. Immune cell crosstalk in type 1 diabetes. *Nat Rev Immunol.* 2010; 10:501-513.

40. Sharif S, Arreaza G A, Zucker P, Mi Q S, Sondhi J, Naidenko O V, Kronenberg M, Koezuka Y, Delovitch T L, Gombert J M, Leite-De-Moraes M, Gouarin C, Zhu R, Hameg A, Nakayama T, Taniguchi M, Lepault F, Lehuen A, Bach J F, Herbelin A. Activation of natural killer T cells by alpha-galactosylceramide treatment prevents the onset and recurrence of autoimmune Type 1 diabetes. *NatMed.* 2001; 7:1057-1062.

41. Kjer-Nielsen L, Patel O, Corbett A J, Le Nours J, Meehan B, Liu L, Bhati M, Chen Z, Kostenko L, Reantragoon R, Williamson N A, Purcell A W, Dudek N L, McConville M J, O'Hair R A, Khairallah G N, Godfrey D I, Fairlie D P, Rossjohn J, McCluskey J. MR1 presents microbial vitamin B metabolites to MAIT cells. *Nature.* 2012; 491: 717-723.

42. Le Bourhis L, Guerri L, Dusseaux M, Martin E, Soudais C, Lantz O. Mucosal-associated invariant T cells: unconventional development and function. *Trends Immunol.* 2011; 32:212-218.

43. Le Bourhis L, Mburu Y K, Lantz O. MAIT cells, surveyors of a new class of antigen: development and functions. *Curr Opin Immunol.* 2013; 25:174-180.

44. Di Lorenzo T P, Peakman M, Roep B O. Translational mini-review series on type 1 diabetes: Systematic analysis of T cell epitopes in autoimmune diabetes. *Clin Exp Immunol.* 2007; 148:1-16.

45. Ghetie V, Ward E S. FcRn: the MHC class I-related receptor that is more than an IgG transporter. *Immunol Today.* 1997; 18:592-598.

46. Simister N E, Mostov K E. An Fc receptor structurally related to MHC class I antigens. *Nature.* 1989; 337:184-187.

47. Raghavan M, Chen M Y, Gastinel L N, Bjorkman P J. Investigation of the interaction between the class I MHC-related Fc receptor and its immunoglobulin G ligand. *Immunity.* 1994; 1:303-315.

48. Roux K H, Strelets L, Brekke O H, Sandlie I, Michaelsen T E. Comparisons of the ability of human IgG3 hinge mutants, IgM, IgE, and IgA2, to form small immune complexes: a role for flexibility and geometry. *J Immunol.* 1998; 161:4083-4090.

49. Mi W, Wanjie S, Lo S T, Gan Z, Pickl-Herk B, Ober R J, Ward E S. Targeting the neonatal fc receptor for antigen delivery using engineered fc fragments. *J Immunol.* 2008; 181:7550-7561.

50. Yeung Y A, Leabman M K, Marvin J S, Qiu J, Adams C W, Lien S, Starovasnik M A, Lowman H B. Engineering human IgG1 affinity to human neonatal Fc receptor: impact of affinity improvement on pharmacokinetics in primates. *J Immunol.* 2009; 182:7663-7671.

51. Zalevsky J, Chamberlain A K, Horton H M, Karki S, Leung I W, Sproule T J, Lazar G A, Roopenian D C, Desjarlais J R. Enhanced antibody half-life improves in vivo activity. *Nat Biotechnol.* 2010; 28:157-159.

52. Sockolosky J T, Tiffany M R, Szoka F C. Engineering neonatal Fc receptor-mediated recycling and transcytosis in recombinant proteins by short terminal peptide extensions. *Proc Natl Acad Sci USA.* 2012; 109:16095-16100.

53. Mallone R, Culina S. Of bugs and men: antigen-fortified *Lactoccoccus lactis* for type 1 diabetes immunotherapy. *Diabetes.* 2014; 63:2603-2605.

54. Robert S, Gysemans C, Takiishi T, Korf H, Spagnuolo I, Sebastiani G, Van Huynegem K, Steidler L, Caluwaerts S, Demetter P, Wasserfall C H, Atkinson M A, Dotta F, Rottiers P, Van Belle T L, Mathieu C. Oral delivery of Glutamic Acid Decarboxylase (GAD)-65 and IL10 by *Lactococcus lactis* reverses diabetes in recent-onset NOD mice. *Diabetes.* 2014.

55. Takiishi T, Korf H, Van Belle T L, Robert S, Grieco F A, Caluwaerts S, Galleri L, Spagnuolo I, Steidler L, Van Huynegem K, Demetter P, Wasserfall C, Atkinson M A, Dotta F, Rottiers P, Gysemans C, Mathieu C. Reversal of autoimmune diabetes by restoration of antigen-specific tolerance using genetically modified *Lactococcus lactis* in mice. *J Clin Invest.* 2012; 122:1717-1725.

56. Garboczi D N, Utz U, Ghosh P, Seth A, Kim J, VanTienhoven E A, Biddison W E, Wiley D C. Assembly, specific binding, and crystallization of a human TCR-alpha-beta with an antigenic Tax peptide from human T lymphotropic virus type 1 and the class I MHC molecule HLA-A2. *J Immunol.* 1996; 157:5403-5410.

The invention claimed is:

1. A method for inducing tolerance to a pancreatic beta cell antigen of interest in a subject in need thereof, comprising mucosally administering to the subject a therapeutically effective amount of a recombinant chimeric construct comprising a FcRn targeting moiety and a preproinsulin peptide comprising the pancreatic beta cell antigen.

2. The method of claim 1 wherein the pancreatic beta cell antigen is an auto-antigen, an allergen or a molecule that is exogenously administered for therapeutic purposes.

3. The method of claim 1 wherein the subject is an adult, a pregnant woman or a child.

4. The method of claim 1 wherein the subject is a newborn or a neonate.

5. The method of claim 1 wherein the subject is predisposed or believed to be predisposed to developing, or has already developed or is developing diabetes.

6. The method of claim 1 wherein the subject is predisposed or believed to be predisposed to developing, or has already developed or is developing an immune response to an insulin antigen expressed by pancreatic beta cells.

7. The method of claim 1 wherein the subject is predisposed or believed to be predisposed to developing, or has already developed or is developing an immune reaction against insulin that is exogenously administered for therapeutic or other purposes.

8. The method of claim 1 wherein the FcRn targeting moiety is an Fc of an IgG antibody or a portion of the Fc.

9. The method of claim 1 wherein the recombinant chimeric construct is a fusion protein that comprises an amino acid sequence comprising a portion of an Fc region and an amino acid sequence encoding the preproinsulin peptide.

10. The method of claim 1 wherein the recombinant chimeric construct is administered to the subject by administering recombinant bacteria that express the construct.

11. The method of claim 1 wherein the recombinant chimeric construct is delivered via the oral cavity.

12. The method of claim 1 wherein the recombinant chimeric construct is delivered via the respiratory tract.

13. The method of claim 8, wherein the IgG antibody is an IgG1 antibody or an IgG4 antibody.

* * * * *